US006863072B1

(12) United States Patent
Sinnott et al.

(10) Patent No.: US 6,863,072 B1
(45) Date of Patent: Mar. 8, 2005

(54) SYSTEM AND METHOD FOR ATTACHING SOFT TISSUE TO BONE

(75) Inventors: Mary Sinnott, Logan, UT (US); Dan Gerbec, Logan, UT (US); Alan Chervitz, Palm Harbor, FL (US); T. Wade Fallin, Hyde Park, UT (US)

(73) Assignee: MedicineLodge, Inc., Logan, UT (US)

( * ) Notice: Subject to any disclaimer, the term of this patent is extended or adjusted under 35 U.S.C. 154(b) by 0 days.

(21) Appl. No.: 10/756,445

(22) Filed: Jan. 13, 2004

Related U.S. Application Data

(62) Division of application No. 10/184,703, filed on Jun. 28, 2002.
(60) Provisional application No. 60/301,596, filed on Jun. 28, 2001.

(51) Int. Cl.[7] .......................... A61F 13/06; A61B 17/56
(52) U.S. Cl. ....................... 128/892; 606/73; 623/13.14
(58) Field of Search ............................ 606/72, 73, 232, 606/233; 623/13.14; 128/898

(56) References Cited

U.S. PATENT DOCUMENTS

| 2,741,289 | A | * | 4/1956 | Grow .......................... 411/185 |
|---|---|---|---|---|
| 4,013,071 | A | | 3/1977 | Rosenberg |
| 5,013,316 | A | * | 5/1991 | Goble et al. ................... 606/72 |
| 5,167,664 | A | | 12/1992 | Hodorek |
| 5,375,956 | A | | 12/1994 | Pennig |
| 5,498,265 | A | | 3/1996 | Asnis et al. |
| 5,840,078 | A | * | 11/1998 | Yerys .......................... 606/151 |
| 5,891,168 | A | * | 4/1999 | Thal ............................ 606/232 |
| 6,001,112 | A | * | 12/1999 | Taylor .......................... 606/159 |
| 6,017,346 | A | * | 1/2000 | Grotz ............................ 606/72 |
| 6,056,751 | A | * | 5/2000 | Fenton, Jr. ..................... 606/72 |
| 6,123,711 | A | | 9/2000 | Winters |
| 6,383,187 | B2 | | 5/2002 | Tormala et al. |
| 6,464,706 | B1 | * | 10/2002 | Winters ......................... 606/73 |
| RE37,963 | E | * | 1/2003 | Thal ............................ 606/232 |
| 6,569,186 | B1 | * | 5/2003 | Winters et al. .............. 606/232 |

* cited by examiner

Primary Examiner—Pedro Philogene
Assistant Examiner—D. Austin Bonderer
(74) Attorney, Agent, or Firm—Pandiscio & Pandiscio

(57) ABSTRACT

A system and method for attaching soft tissue to bone. The invention comprises the provision and use of a novel two-part anchor for attaching soft tissue and the like to bone. In one form of the invention, the two-part anchor generally comprises a stake and a cap. The stake is adapted to be positioned in bone and form a stake for impalement by a piece of soft tissue. The cap is adapted to cap soft tissue which has been impaled on the stake and thereby bind the soft tissue to the stake and, hence, to the bone in which the stake is set.

9 Claims, 31 Drawing Sheets

SYSTEM AND METHOD FOR ATTACHING SOFT TISSUE TO BONE

REFERENCE TO PENDING PRIOR PATENT APPLICATION

This is a divisional of pending prior U.S. Pat. No. application Ser. No. 10/184,703, filed Jun. 28, 2002 by Mary Sinnott et al. for SYSTEM AND METHOD FOR ATTACHING SOFT TISSUE TO BONE, which patent application claims benefit of U.S. Provisional Patent Application Ser. No. 60/301,596, filed Jun. 28, 2001 by Mary Sinnott et al for SYSTEM AND METHOD FOR ATTACHING SOFT TISSUE TO BONE.

FIELD OF THE INVENTION

This invention relates to medical devices and procedures in general, and more particularly to systems and methods for attaching soft tissue to bone.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones.

Numerous devices are currently available to re-attach soft tissue to bone. Examples of such currently-available devices include screws, staples, suture anchors and tacks.

In soft tissue re-attachment procedures utilizing screws, the detached soft tissue is typically moved back into its original position over the bone. Then the screw is screwed through the soft tissue and into the bone, with the shank and head of the screw holding the soft tissue to the bone.

Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. Next, the soft tissue is moved into position over the hole containing the deployed suture anchor. As this is done, the free end(s) of the suture is (are) passed through or around the soft tissue, so that the free end(s) of the suture reside(s) on the far (i.e., non-bone) side of the soft tissue. Finally, the suture is used to tie the soft tissue securely to the bone.

Alternatively, in some soft tissue re-attachment procedures utilizing suture anchors of the type described above, the soft tissue may first be moved into position over the bone. Then, while the soft tissue lies in position against the bone, a single hole may be drilled through the soft tissue and into the bone. Next, a suture anchor is passed through the soft tissue and deployed in the bone using an appropriate installation tool. This results in the suture anchor being locked to the bone, with the free end(s) of the suture extending out of the bone and through the soft tissue. Finally, the suture is used to tie the soft tissue securely to the bone.

In some cases, the suture anchor may include drill means at its distal end, whereby the suture anchor can be drilled into the bone, or drilled through the soft tissue and into the bone, whereby the aforementioned drilling and anchor-deployment steps are effectively combined.

Similarly, in soft tissue re-attachment procedures utilizing tacks, the detached soft tissue is typically moved back into its original position over the bone, and then a tack-receiving hole is generally drilled through the soft tissue and into the bone. Then the tack is driven through the soft tissue and into the bone, so that the shaft and head of the tack will hold the soft tissue to the bone.

While systems and methods based on the aforementioned screws, staples, suture anchors and tacks are generally effective, they also all suffer from one or more disadvantages.

SUMMARY OF THE INVENTION

Accordingly, one object of the present invention is to provide a novel system and method for re-attaching soft tissue to bone which improves upon the prior art devices and techniques discussed above.

Another object of the present invention is to provide a novel system and method for re-attaching soft tissue to bone which is easy to use and simple to perform.

And another object of the present invention is to provide a novel system and method for re-attaching soft tissue to bone which expedites and facilitates the reattachment procedure.

Still another object of the present invention is to provide a novel system and method for re-attaching soft tissue to bone which minimizes trauma to the patient during the re-attachment procedure.

Yet another object of the present invention is to provide a novel system and method for re-attaching soft tissue to bone which can be used in both open surgical procedures and in closed surgical procedures (e.g., arthroscopic or endoscopic surgical procedures) where access to the surgical site is provided by one or more cannulas.

And another object of the present invention is to provide a novel system and method for re-attaching soft tissue to bone which is also usable in the attachment of prosthetic devices, and/or grafts of natural and/or synthetic material, to bone or bone-like structures.

These and other objects of the present invention are achieved by the provision and use of a novel two-part anchor for attaching soft tissue and the like to bone. In one form of the invention, the two-part anchor generally comprises a stake and a cap. The stake is adapted to be positioned in bone and form a stake for impalement by a piece of soft tissue. The cap is adapted to cap soft tissue which has been impaled on the stake and thereby bind the soft tissue to the stake and, hence, to the bone in which the stake is set.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
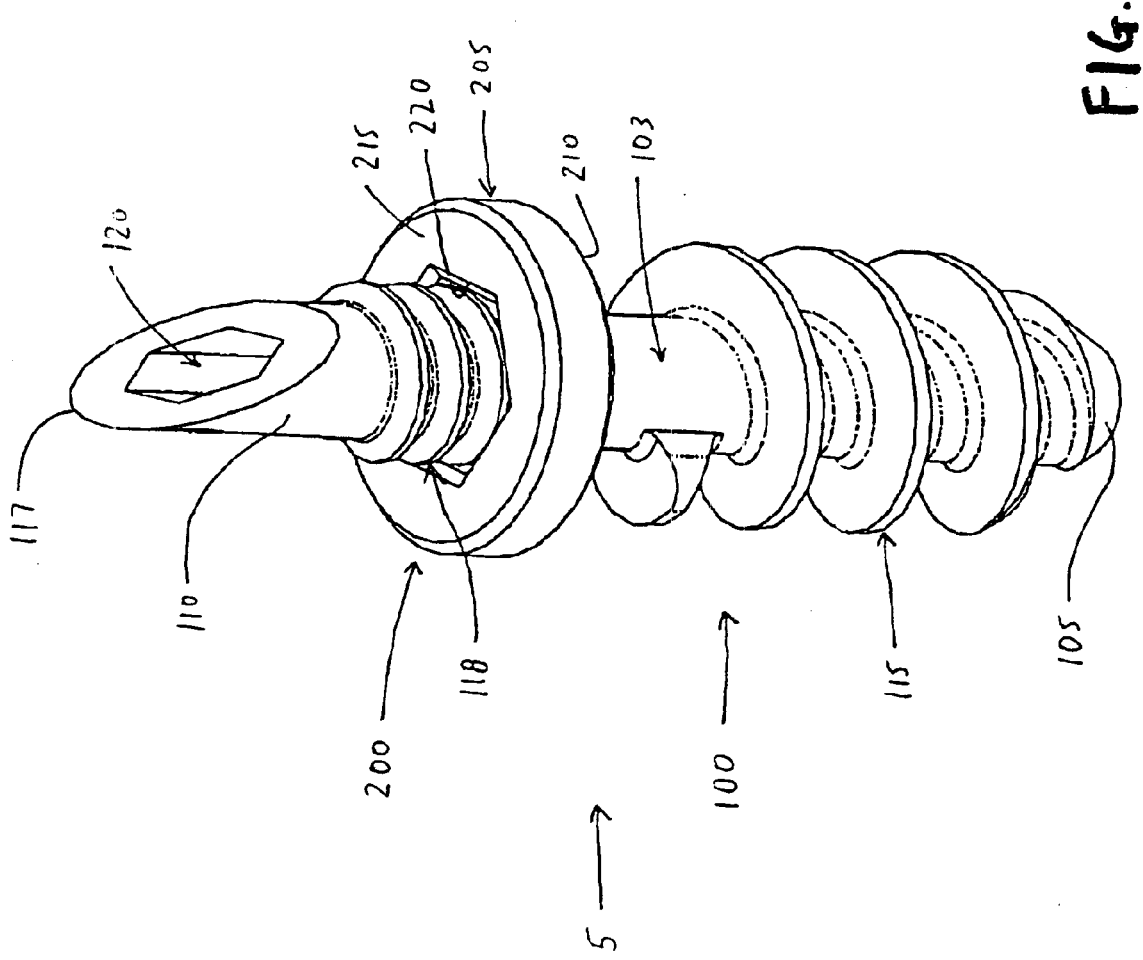
FIG. 1 is a perspective view of a novel two-part anchor formed in accordance with the present invention.
Figure 2:
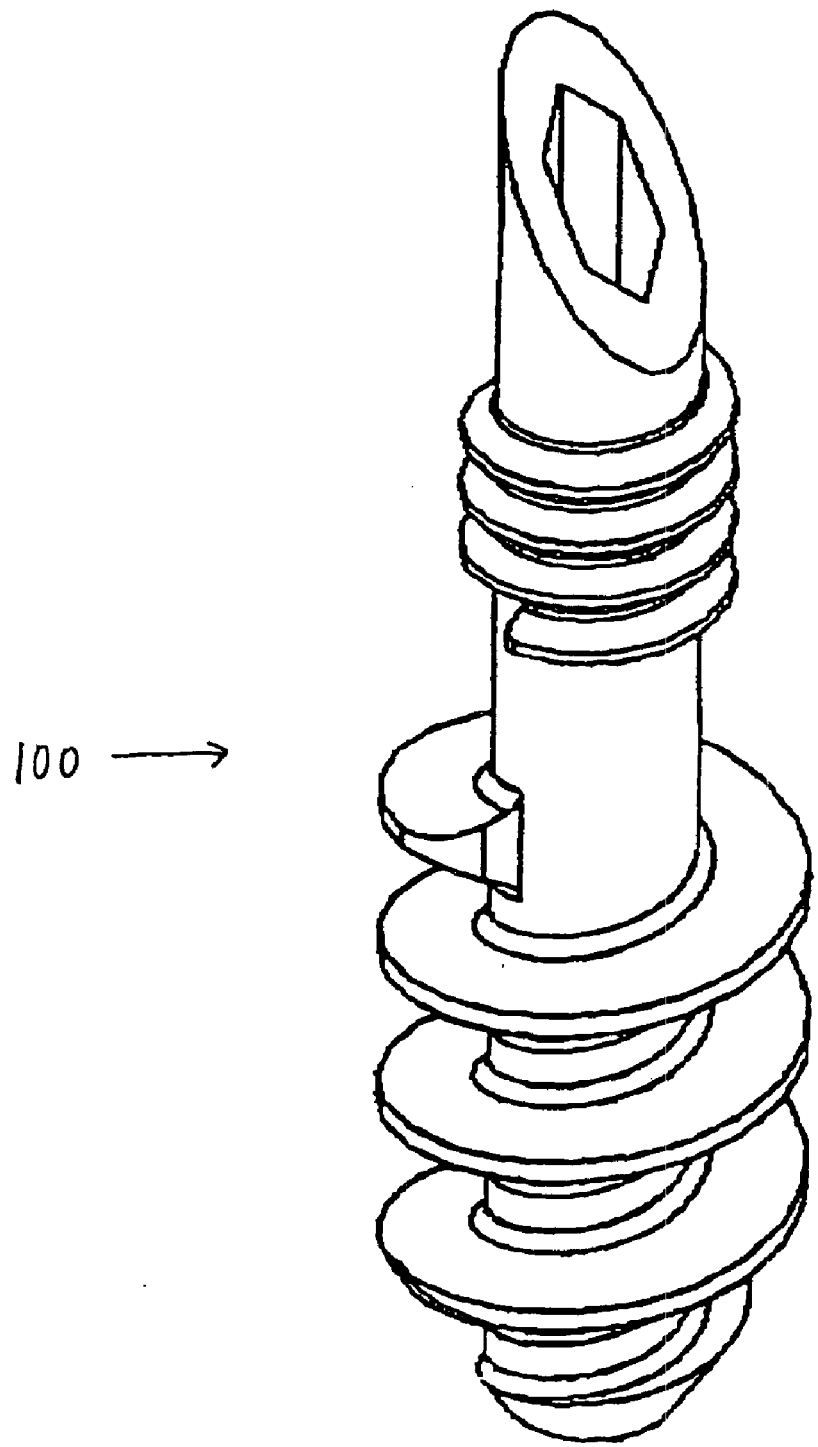
FIG. 2 is a perspective view of the stake used in the two-part anchor shown in FIG. 1.
Figure 3:
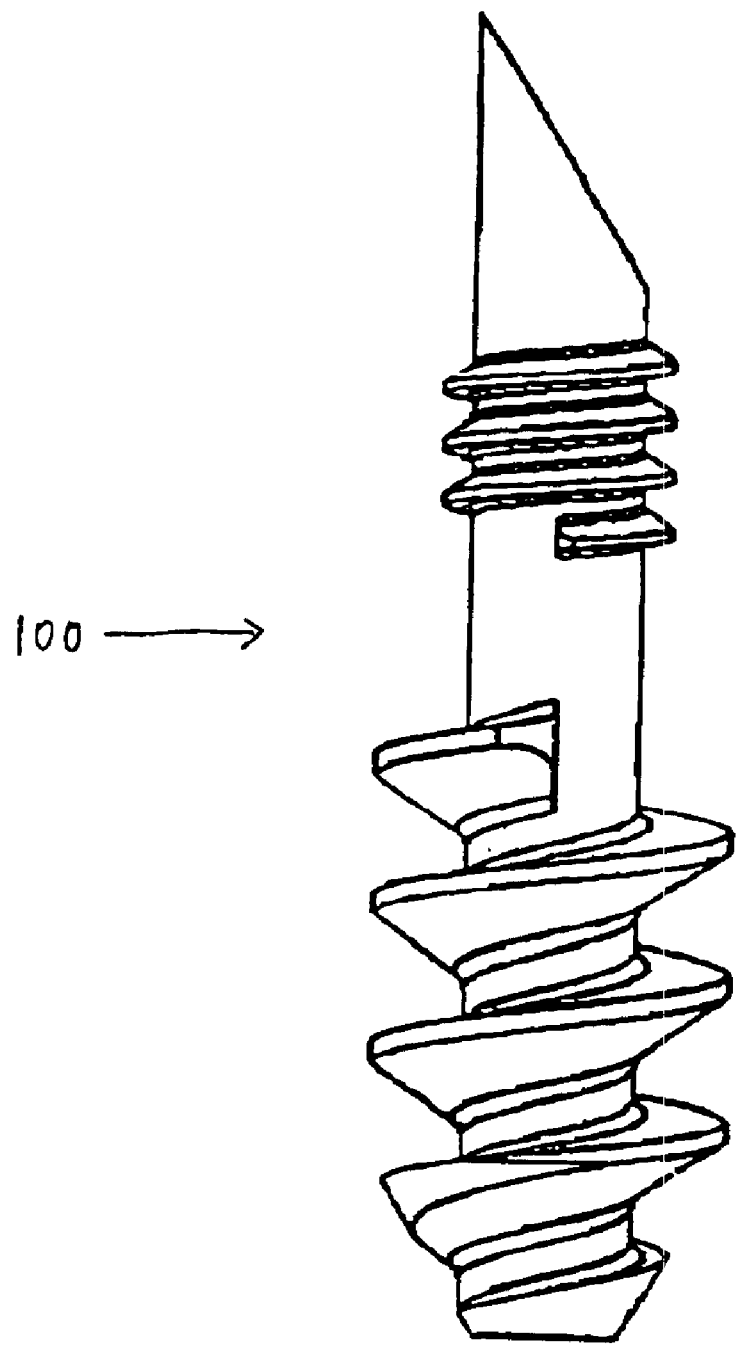
FIG. 3 is a side view of the stake used in the two-part anchor shown in FIG. 1.

Looking first at FIGS. 1–4, there is shown a two-part anchor 5 which generally comprises a stake 100 and a cap 200.

Stake 100 is adapted to be positioned in bone and form a stake for impalement by a piece of soft tissue. To this end, stake 100 generally comprises an elongated body 103 having a distal end 105 and a proximal end 110. Stake 100 has a first exterior thread 115 formed on the distal end thereof. Thread 115 preferably begins at the stake's distal end 105 and extends for approximately half of the total length of the stake. Thread 115 is preferably a buttress thread to initially facilitate turning stake 100 into bone and to thereafter resist a pulling withdrawal of stake 100 from bone. The proximal end 110 of stake 100 terminates in a sharp point 117. Intermediate first exterior thread 115 and sharp point 117 is a second exterior thread 118. Second exterior thread 118 is also a buttress thread, but oriented with a reverse orientation from that of the aforementioned first exterior thread 115, such that thread 118 will initially facilitate the pushing insertion of cap 200 thereover and to thereafter resist a pulling withdrawal of cap 200 from stake 100. Stake 100 also comprises a passageway 120. Passageway 120 opens on the proximal end 110 of stake 100 and preferably extends for substantially the entire length of stake 100. Passageway 120 has a non-circular cross-section, such that the passageway may receive a driving tool therein and stake 100 may thereafter be turned by the driving tool so as to set stake 100 into bone. By way of example but not limitation, passageway 120 may comprise a hexagonal cross-section, such that stake 100 may be turned by a hexagonal driver of the sort generally known in the orthopedic arts.

Cap 200 is adapted to cap soft tissue which has been impaled on stake 100 and thereby bind the soft tissue to the stake 100 and, hence, to the bone in which stake 100 is set. To this end, cap 200 generally comprises a flat body 205 having a distal end 210 and a proximal end 215. A passageway 220 opens on the proximal end 215 of cap 200 and extends completely through cap 200, whereby cap 200 can be pushed over the proximal end 110 of stake 100 once tissue has been impaled on the stake, with the distal end 210 of cap 200 engaging the top surface of the tissue impaled on stake 100. If necessary, cap 200 can be removed from stake 100 by unscrewing the cap from the stake.

Figure 4:
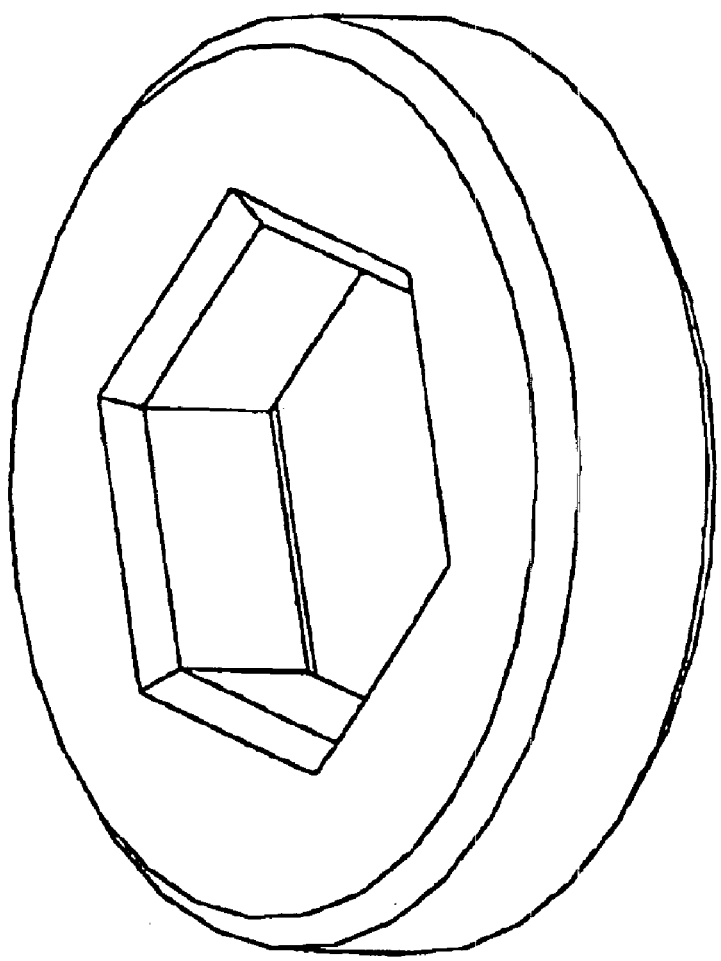
FIG. 4 is a perspective view of the cap used in the two-part anchor shown in FIG. 1.
Figure 5:
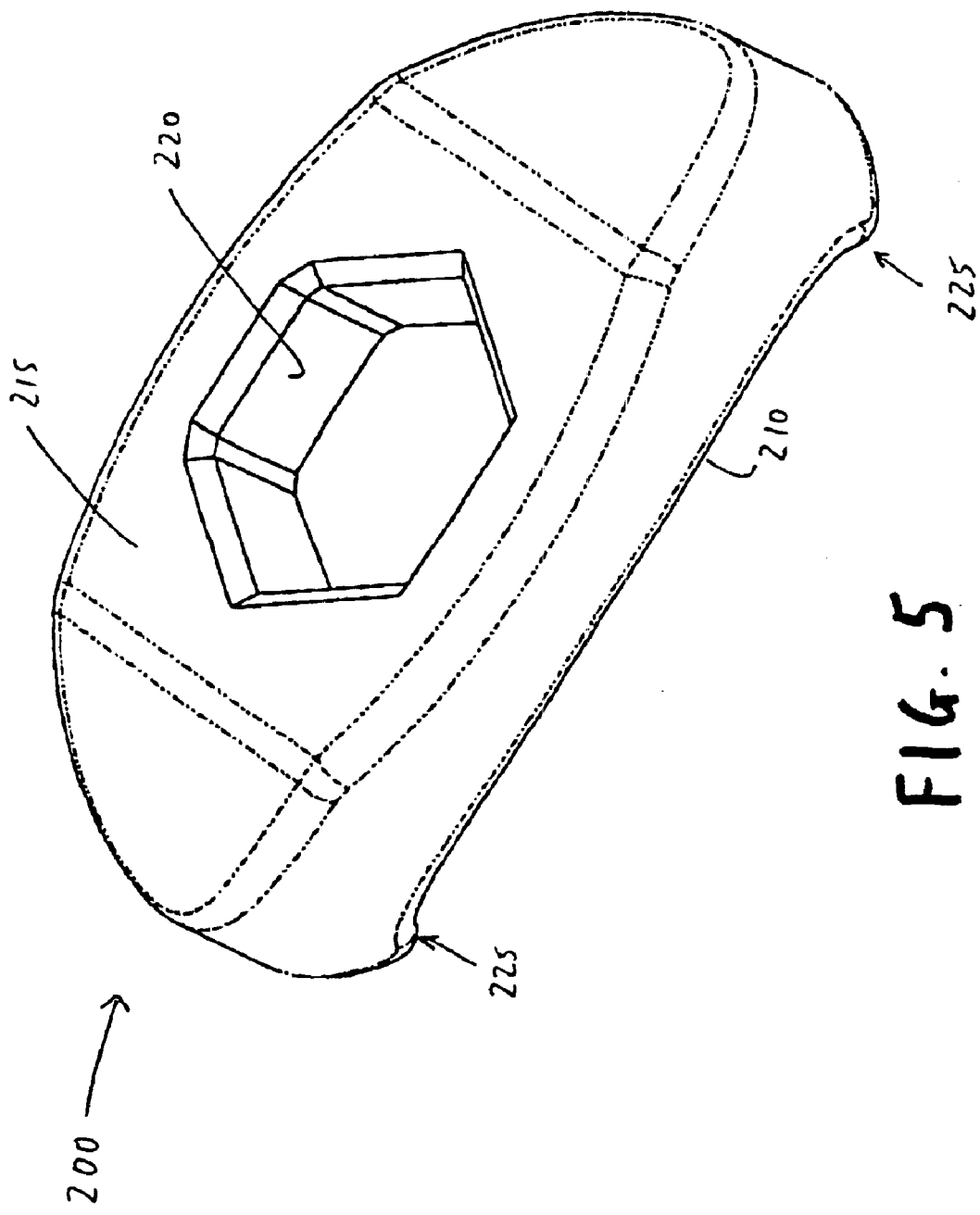
FIG. 5 is a perspective view of an alternative form of cap.
Figure 6:
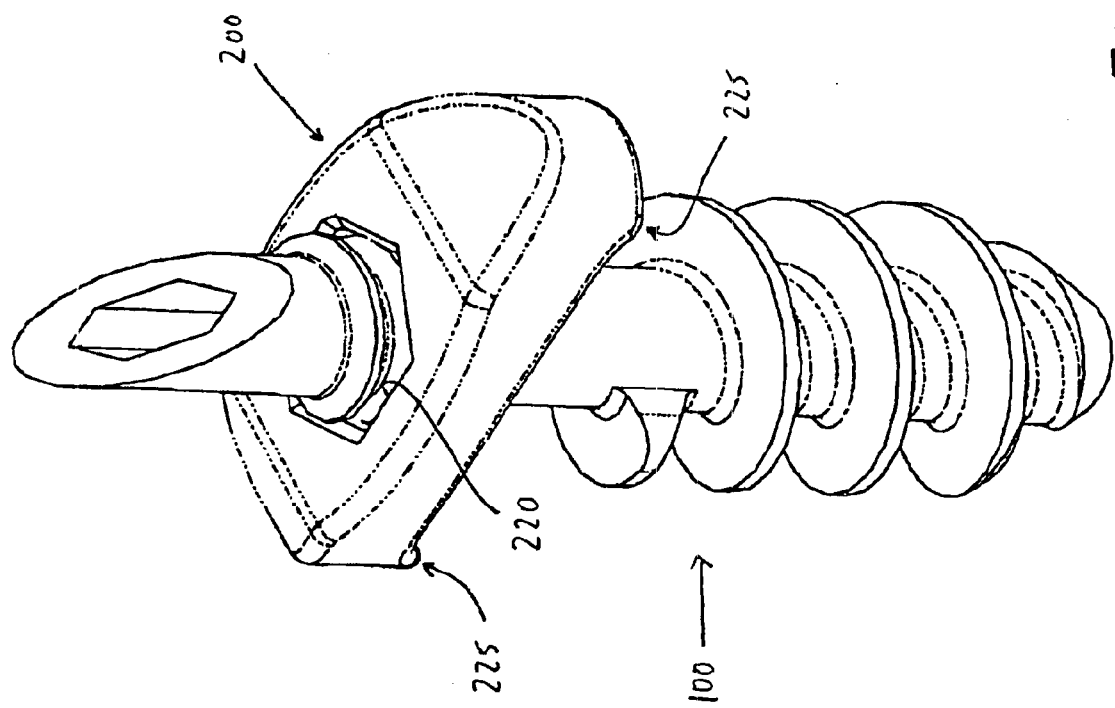
FIG. 6 is a perspective view showing the cap of FIG. 5 mounted on the stake shown in FIG. 2.

In FIG. 4, cap 200 is shown as having a substantially round profile when viewed in end view. However, if desired, cap 200 may have a substantially elliptical profile such as is shown in FIGS. 5 and 6, and may have two or more distally projecting feet 225 formed thereon for engaging tissue captured distal to the cap.

Figure 7:
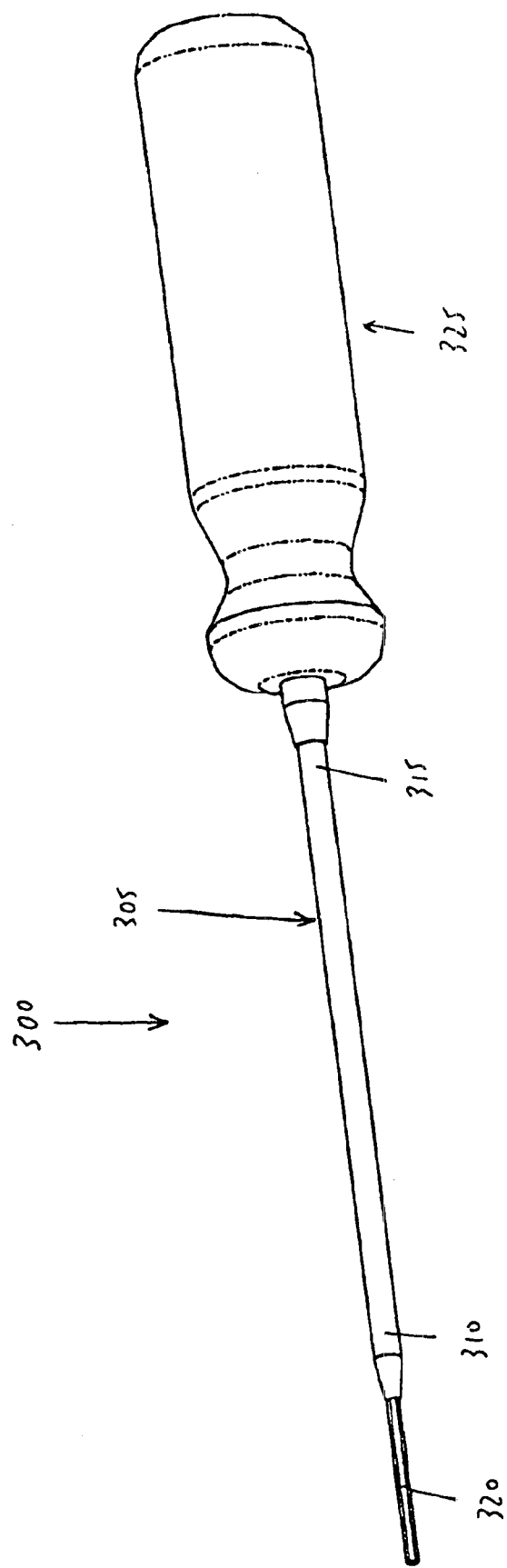
FIG. 7 is a stake inserter formed in accordance with the present invention.
Figure 8:
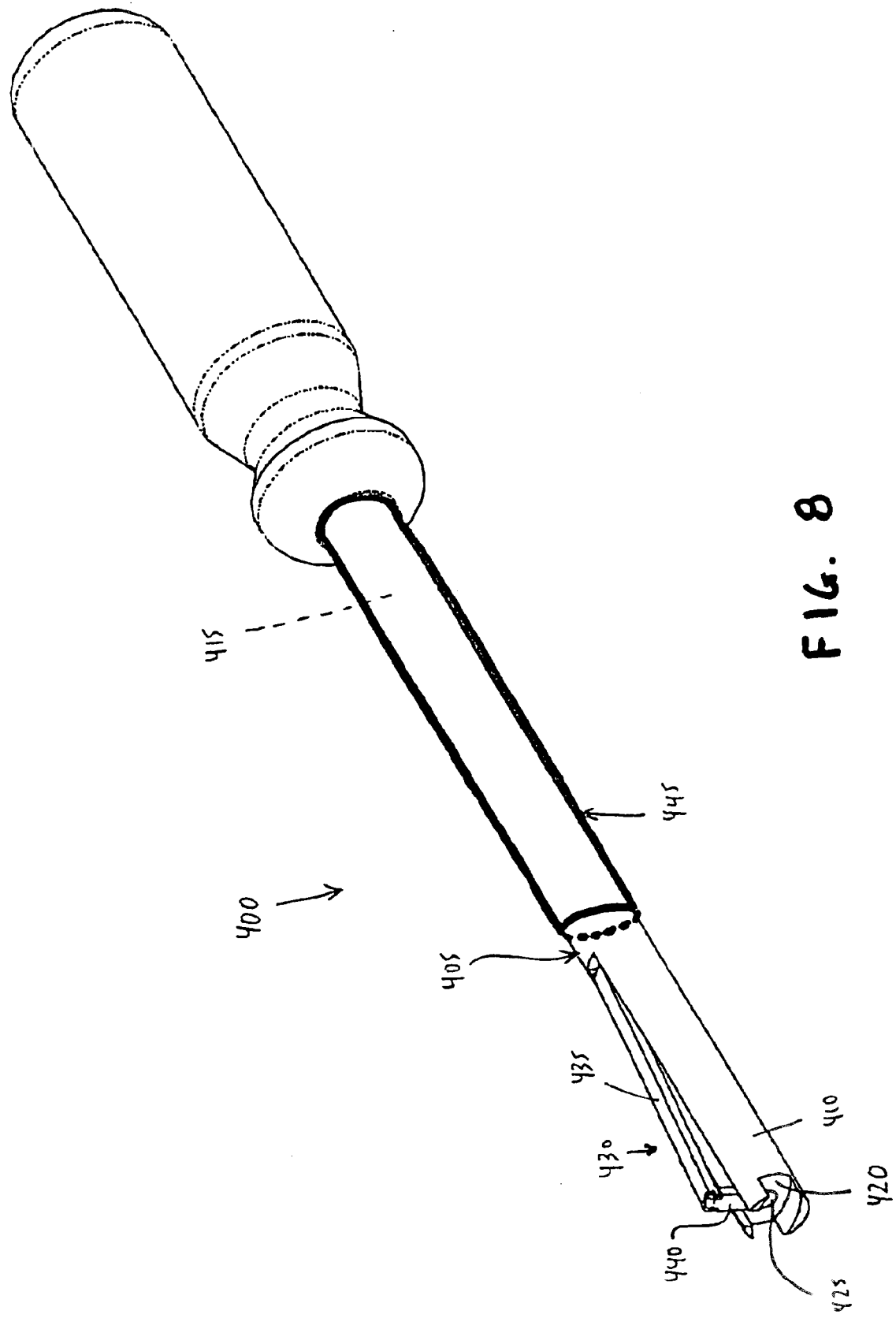
FIGS. 8–21 are a series of views showing a cap inserter adapted for use with the cap shown in FIG. 5.
Figure 9:
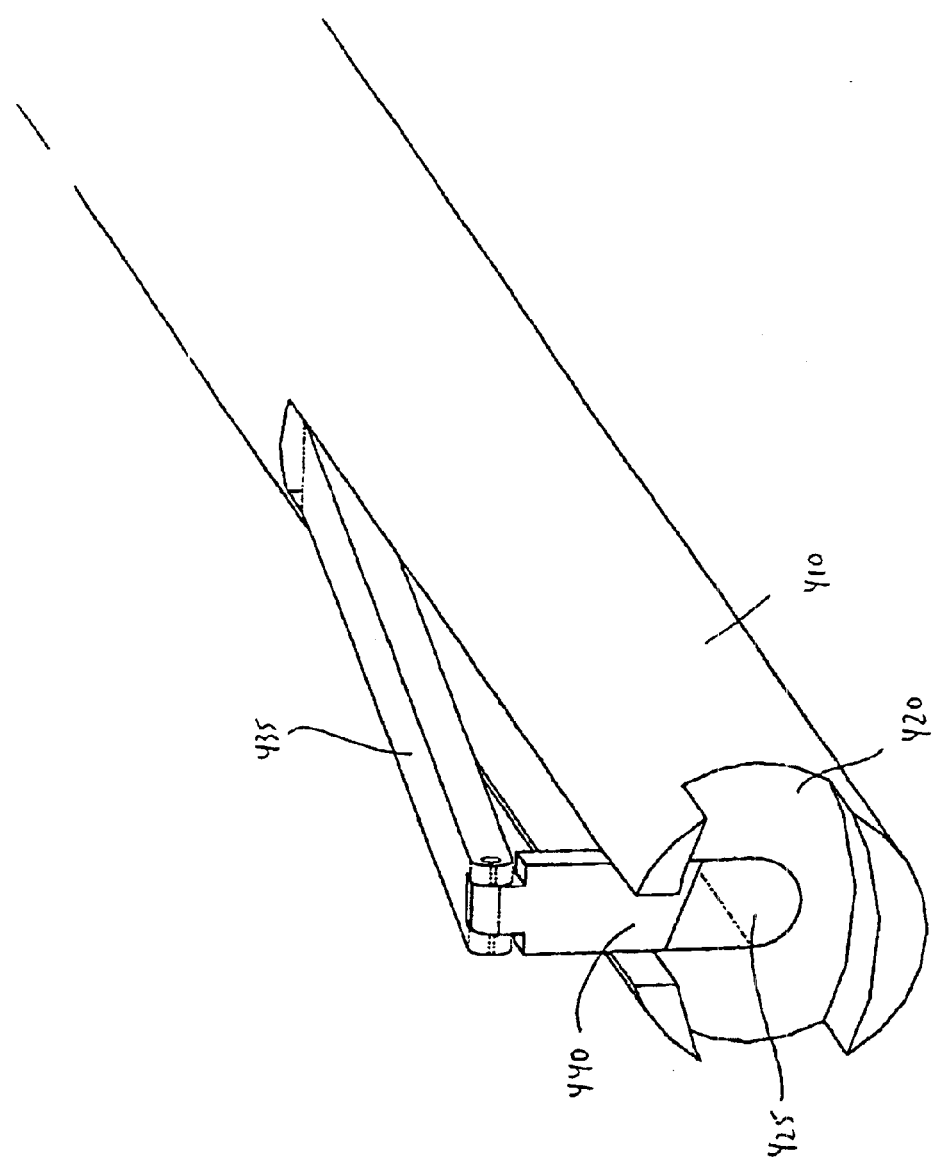
Figure 10:
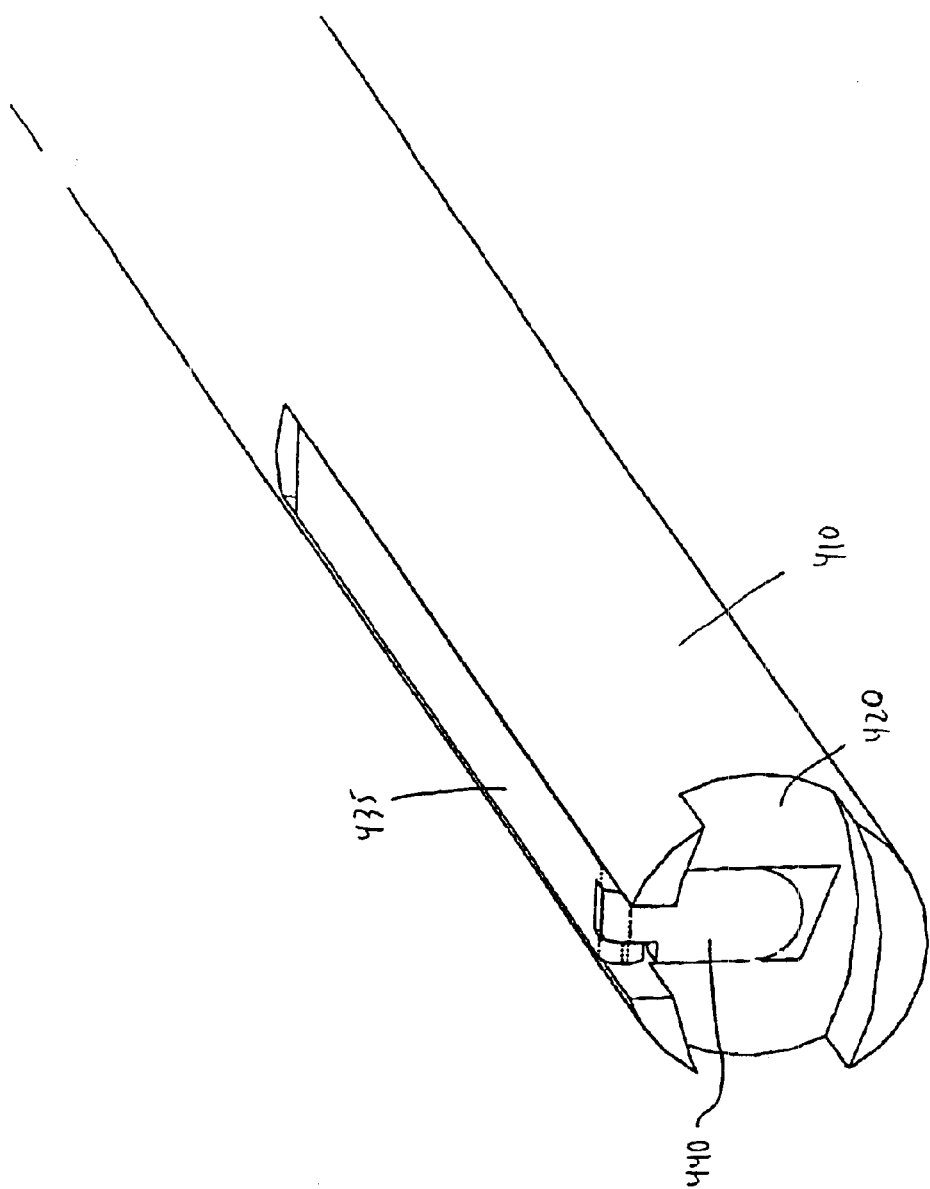
Figure 11:
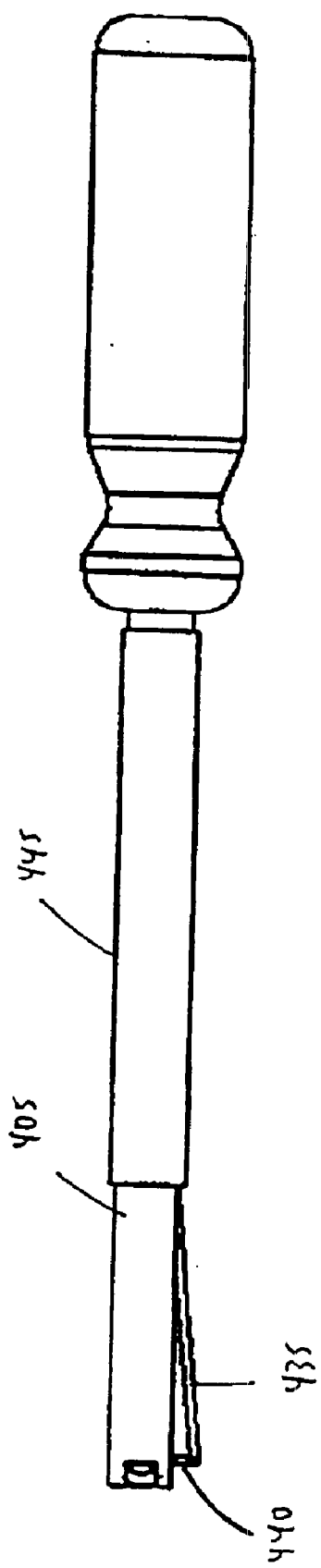
Figure 12:
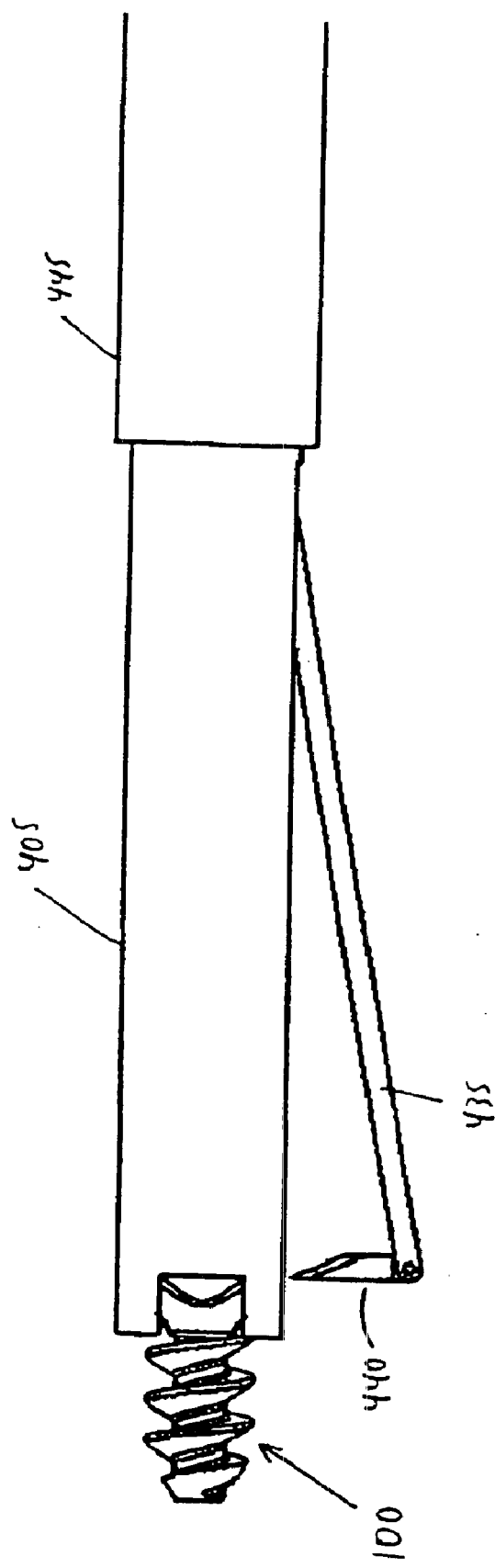
Figure 13:
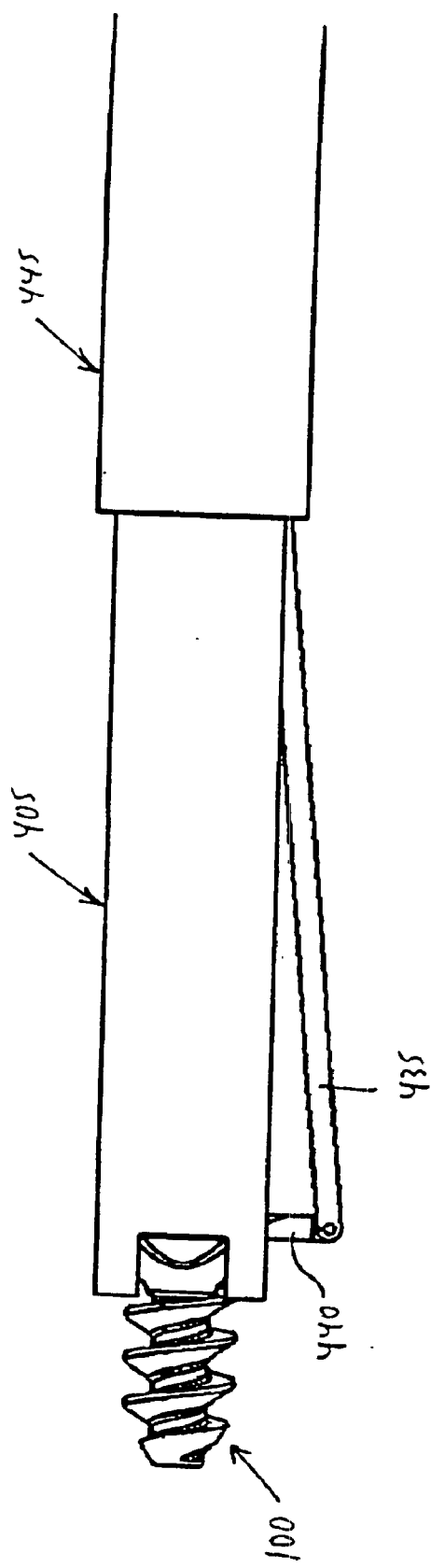
Figure 14:
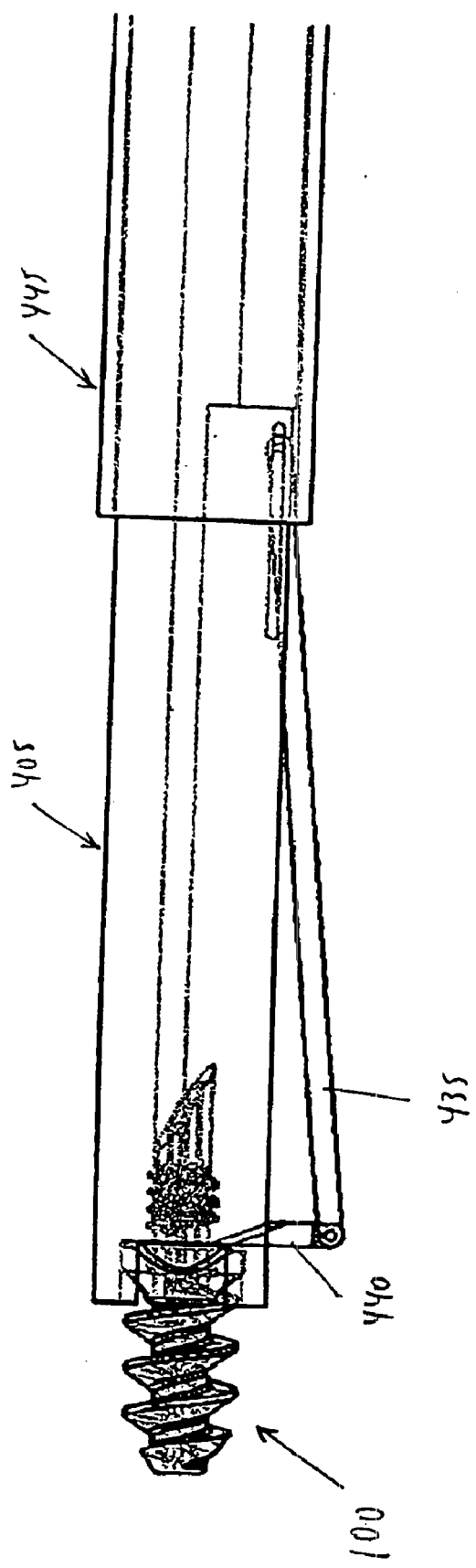
Figure 15:
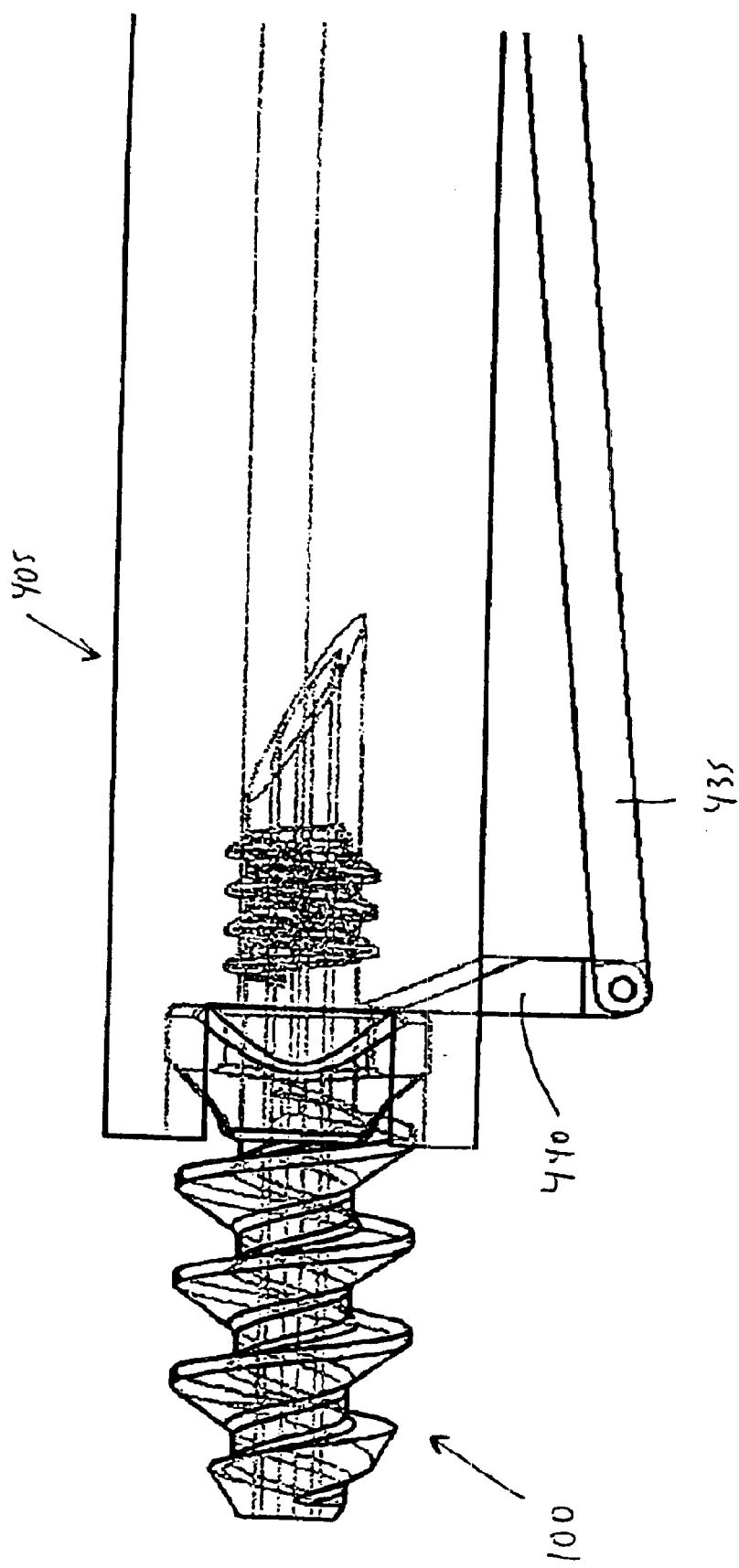
Figure 16:
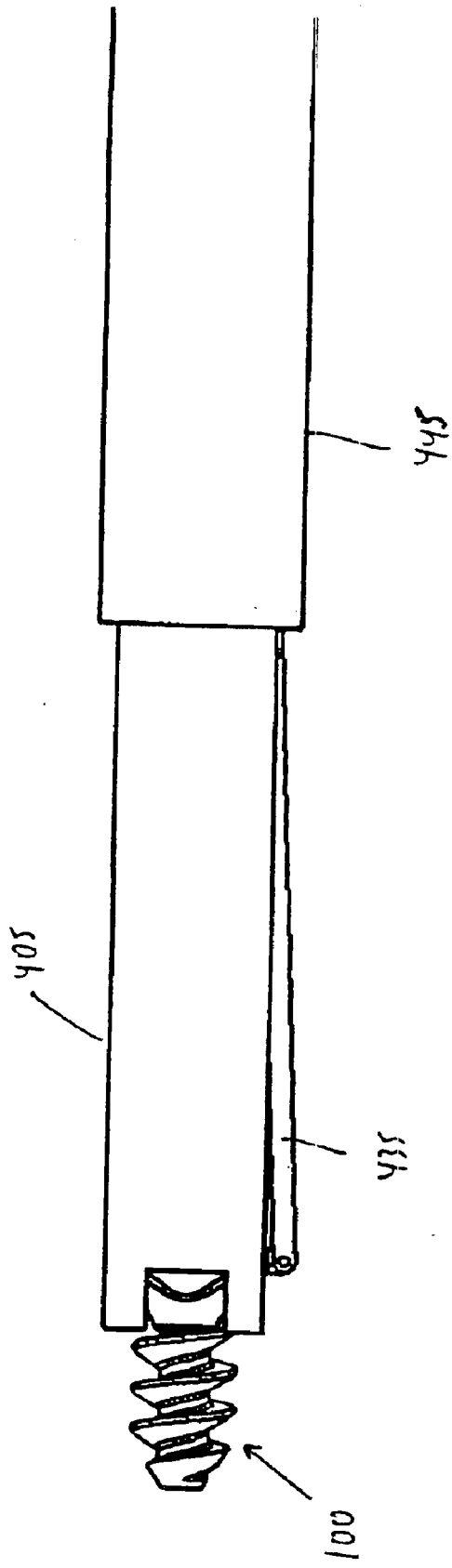
Figure 17:
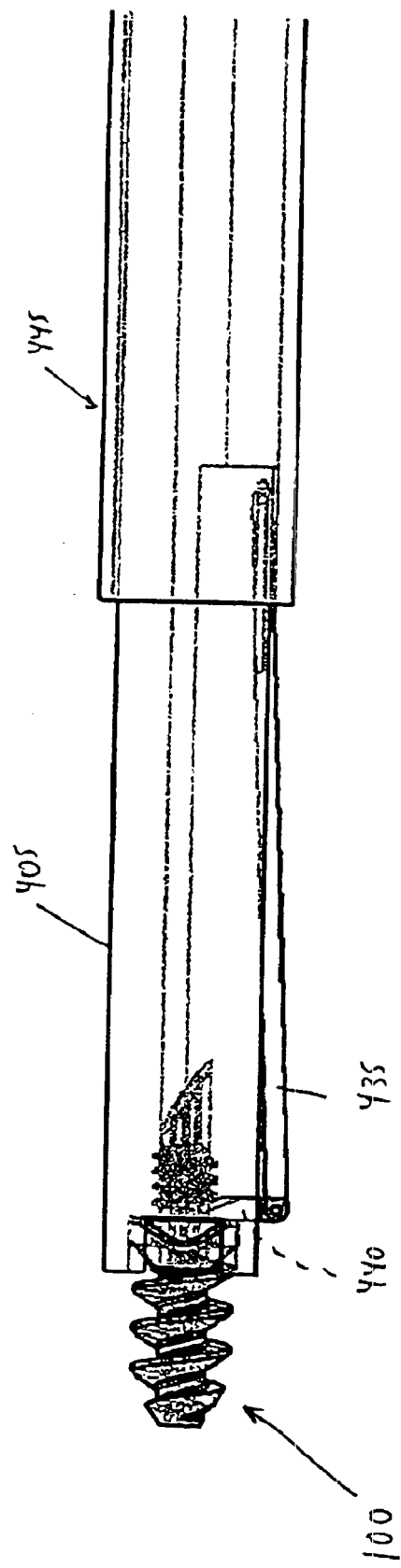
Figure 18:
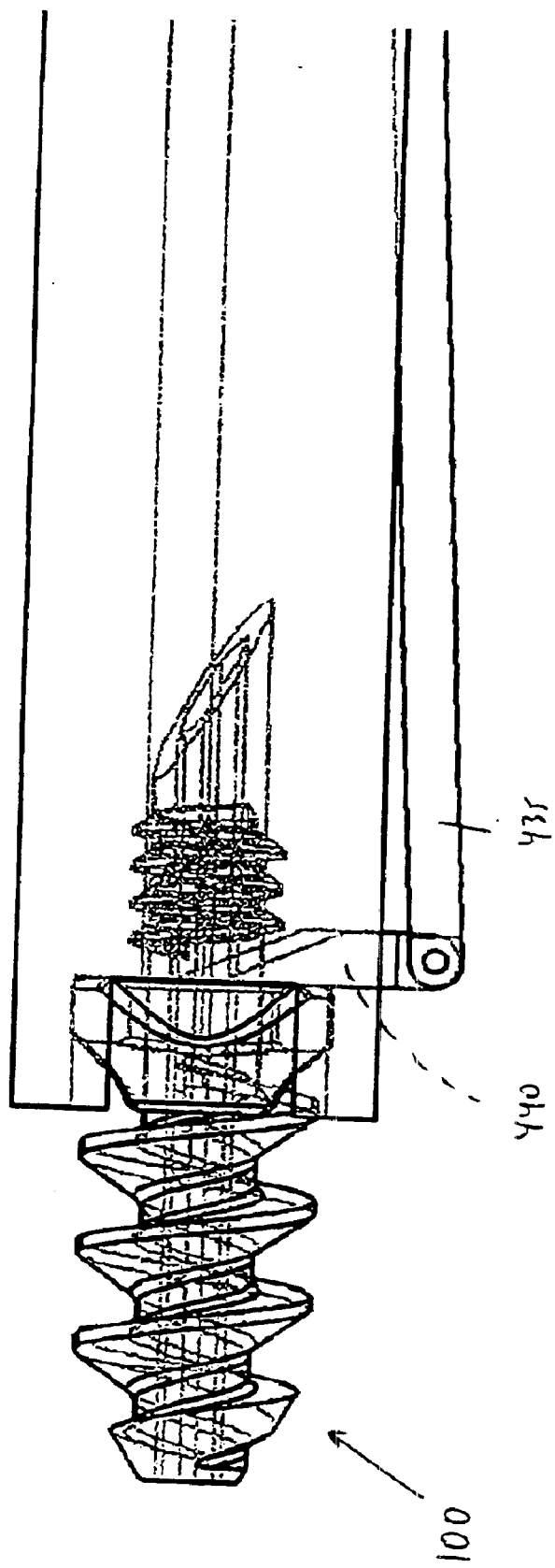
Figure 19:
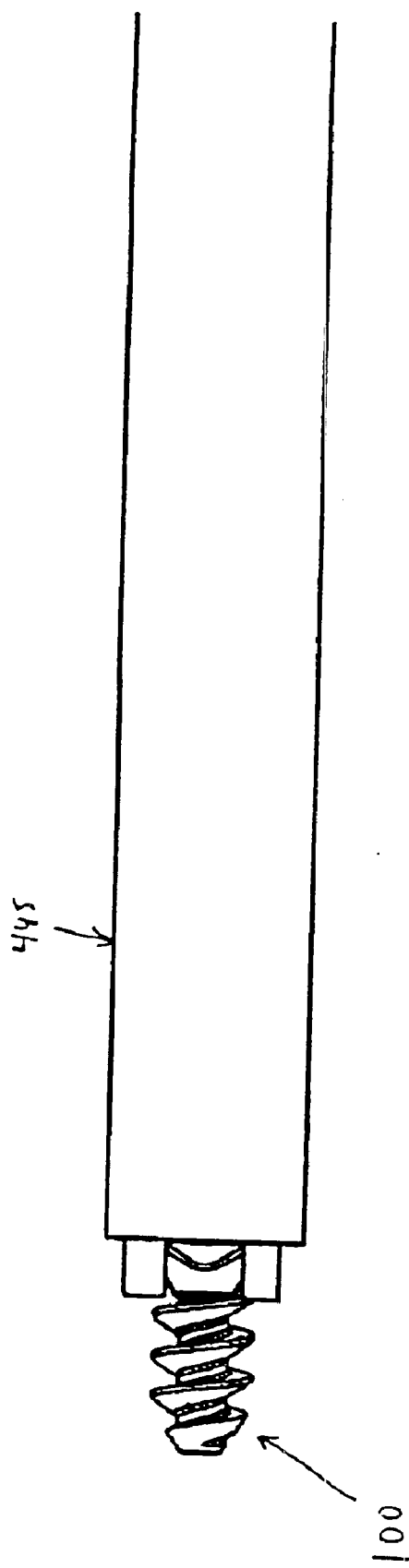
Figure 20:
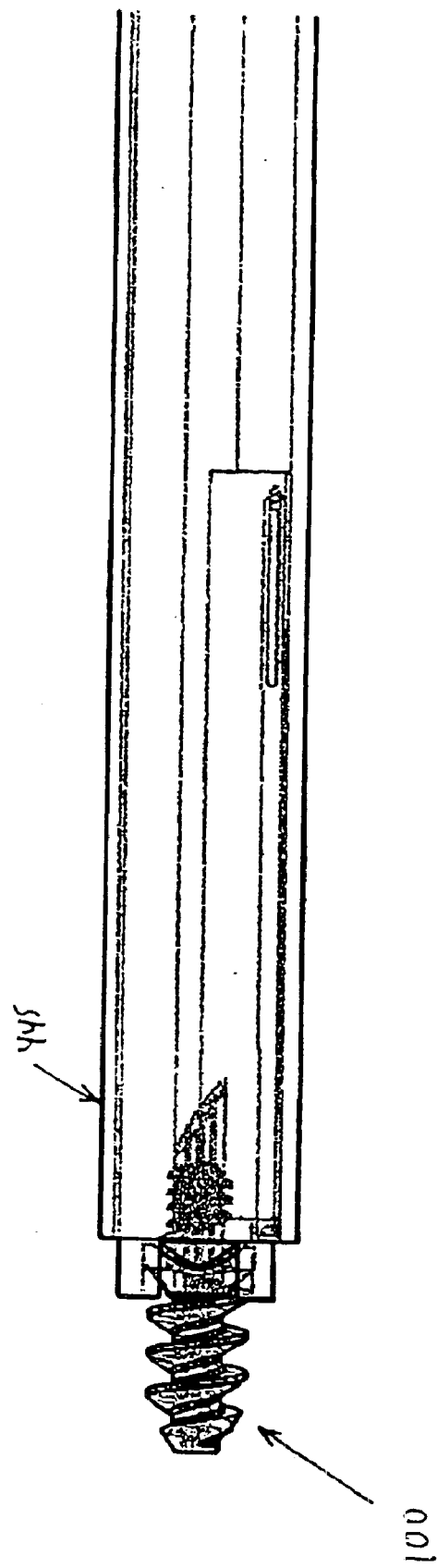
Figure 21:
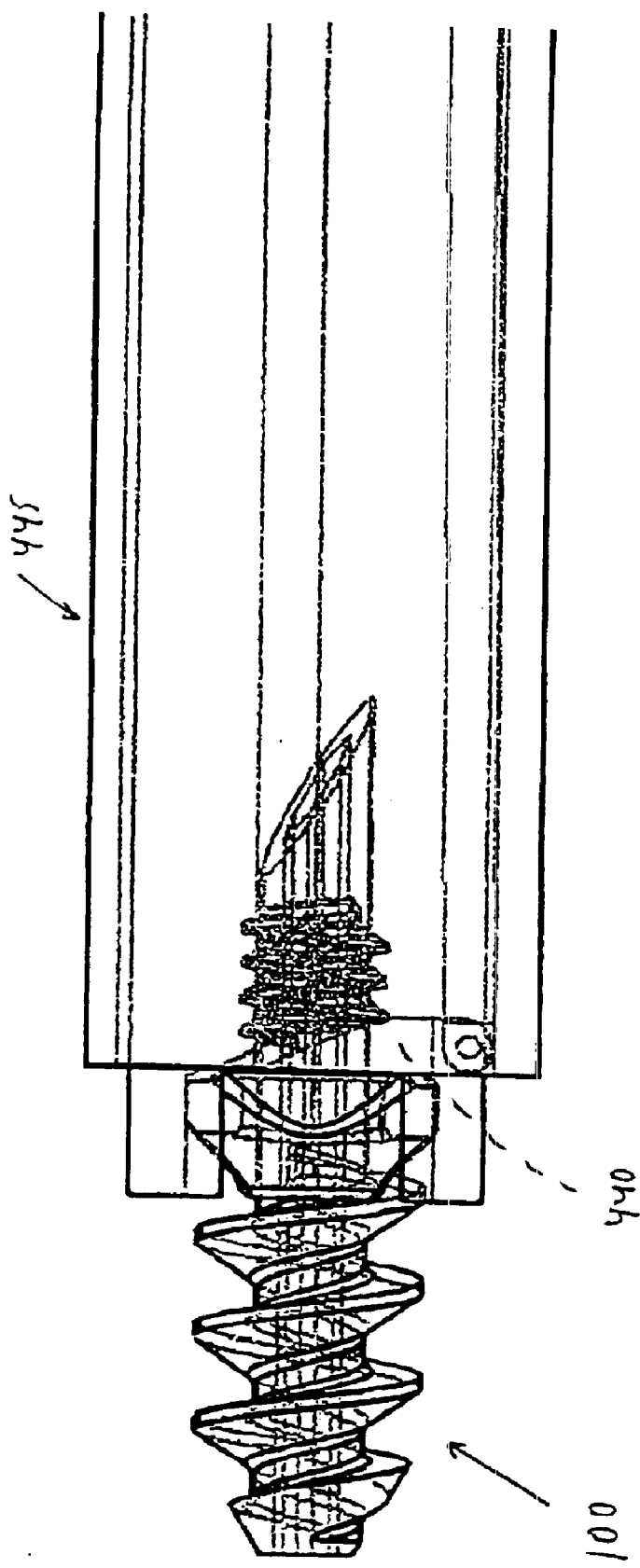

Looking next at FIG. 7, there is shown a stake inserter 300 which is adapted to set stake 100 into bone. Stake inserter 300 generally comprises a shaft 305 having a distal end 310 and a proximal end 315. A tip 320 extends distally from the shaft's distal end 310. Tip 320 has as non-circular cross-sectional configuration corresponding to the non-circular cross-sectional configuration of the passageway 120 of stake 100, whereby tip 320 can be inserted into passageway 120 and transfer rotary motion of stake inserter 300 to stake 100. The tip 320 of stake inserter 300 is preferably long enough to drive stake 100 over the entire length of stake 100, whereby to spread torsional loads over the entire stake 100. If desired, tip 320 may be formed long enough to extend out of the end of stake 100, and may be formed with a share distal tip; in this event, it may be possible to set stake 100 in some types of bone without pre-drilling the bone. Stake inserter 300 also comprises a handle 325 which is secured to the proximal end 315 of shaft 305, whereby stake inserter 300 may be turned by a surgeon.

Looking next at FIGS. 8–21, there is shown a cap inserter 400 which is adapted to set cap 200 onto the sharpened proximal end of the stake after tissue has been impaled on the stake. Cap inserter 400 generally comprises a shaft 405 having a distal end 410 and a proximal end 415. A first recess 420 is formed in distal end 410 and is sized and shaped to receive cap 200 therein. By way of example, cap inserter 400 shown in FIGS. 8–21 has a substantially elliptically-shaped recess 420 formed therein, wherein the cap inserter may receive the elliptical cap of FIGS. 5 and 6 therein. Cap inserter 400 also comprises a second recess 425 formed in its distal end 410. Second recess 425 is sized and shaped to receive the proximal end of a stake 100 when cap inserter 100 is deploying a cap 200 on a stake 100 and trimming off the proximal end of the stake, as will hereinafter be described.

Cap inserter 400 also comprises a guillotine cutter assembly 430 which is adapted to trim off the sharp proximal end of stake 100 after cap 200 has been installed thereon. Guillotine cutter 430 comprises an arm 435 which is pivotally attached to shaft 405, and a blade 440 which is connected to arm 435 and adapted to move radially inwardly as arm 435 is forced parallel to the longitudinal axis of shaft 405. An outer tube 445 is placed concentrically around shaft 405; forcing outer tube 445 distally forces blade 440 radially inwardly, so as to cut off the sharp proximal end of a stake extending into the inserter's second recess 425. FIGS. 8–21 illustrate the structure and operation of the cutter assembly 430. In FIGS. 14, 15, 17, 18, 20 and 21, the distal extent of the stake threads 118 is shortened for clearer illustration of the cap inserter tool second recess.

Two-part anchor 5 may be used as follows.

Figure 22:
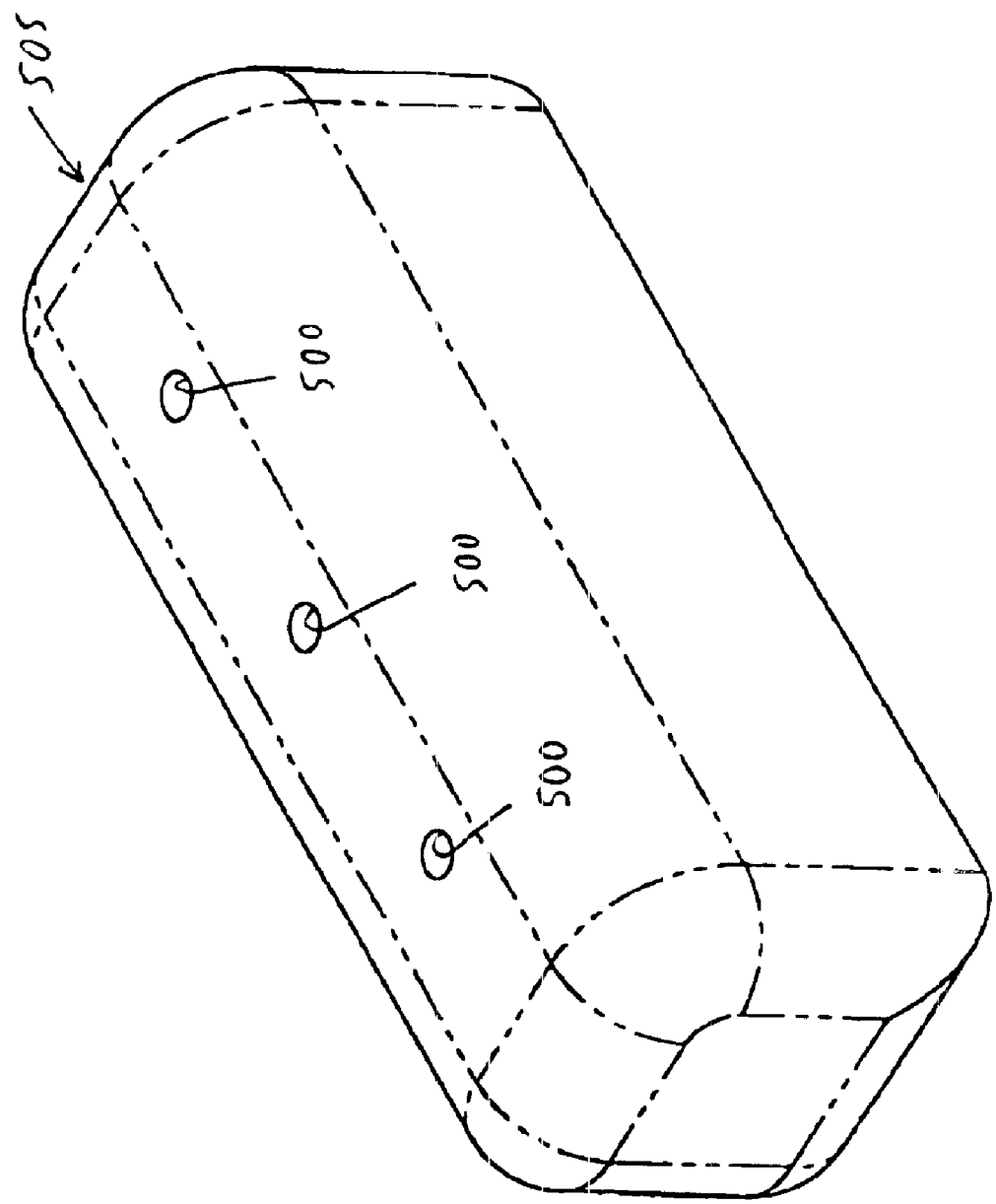
FIGS. 22–31 are a series of views showing the two-part anchor of FIG. 6 securing soft tissue to bone.
Figure 23:
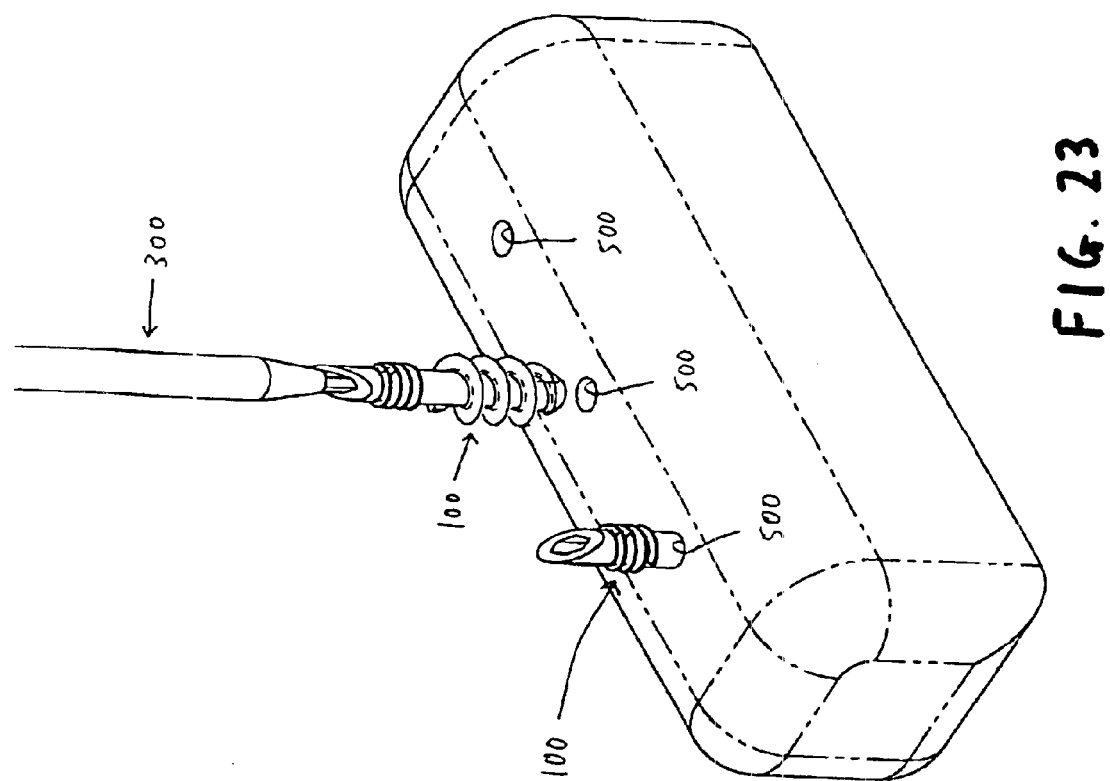
Figure 24:
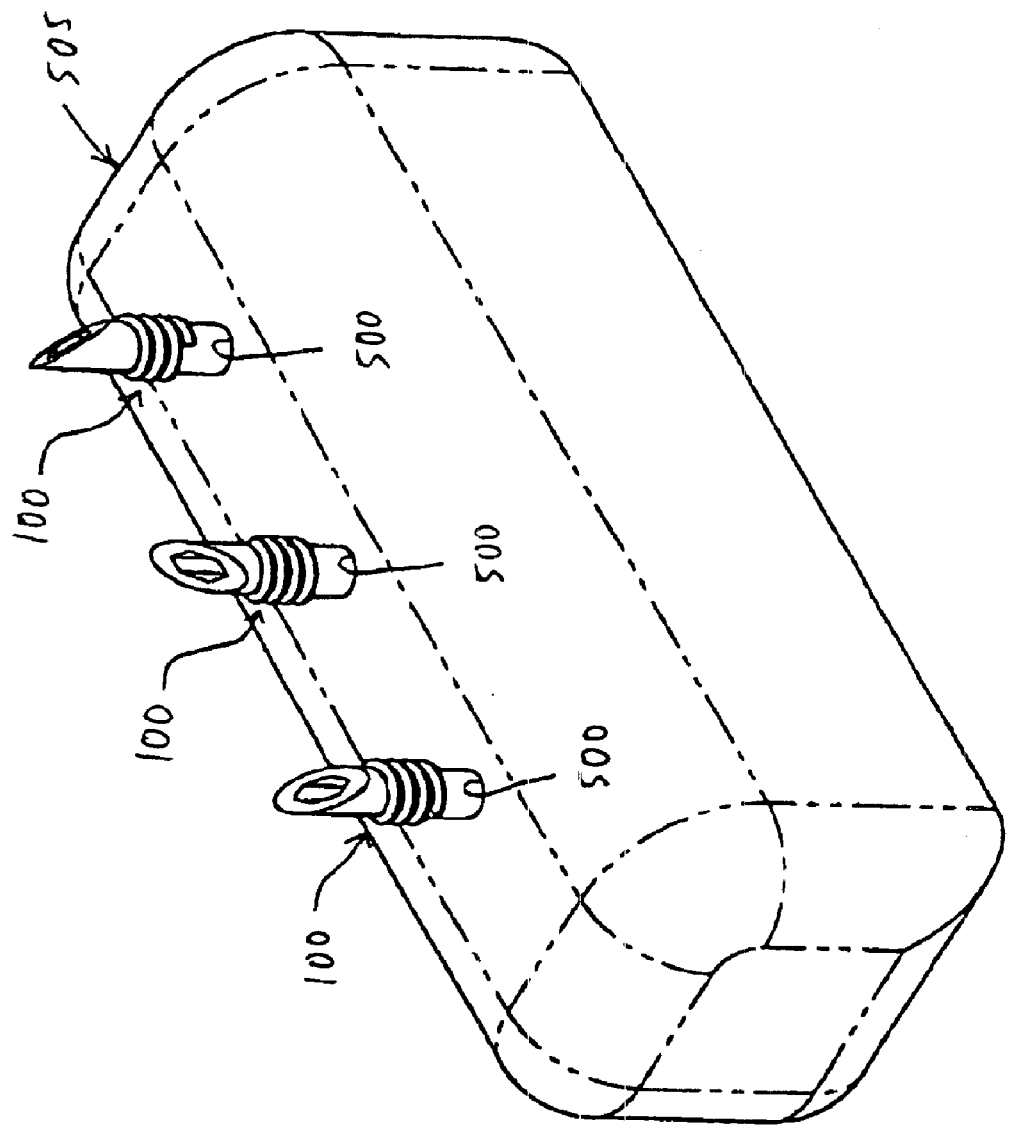
Figure 25:
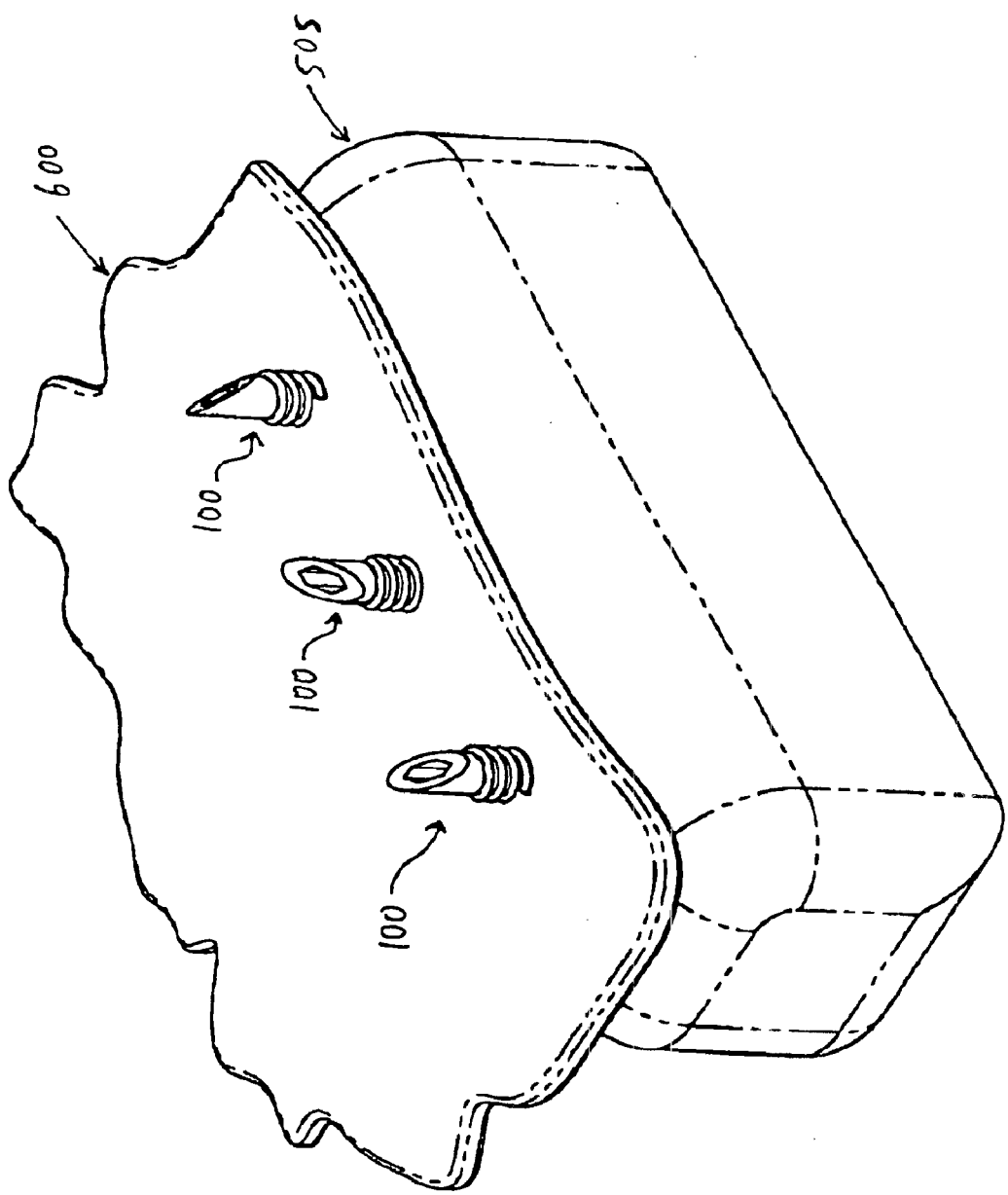
Figure 26:
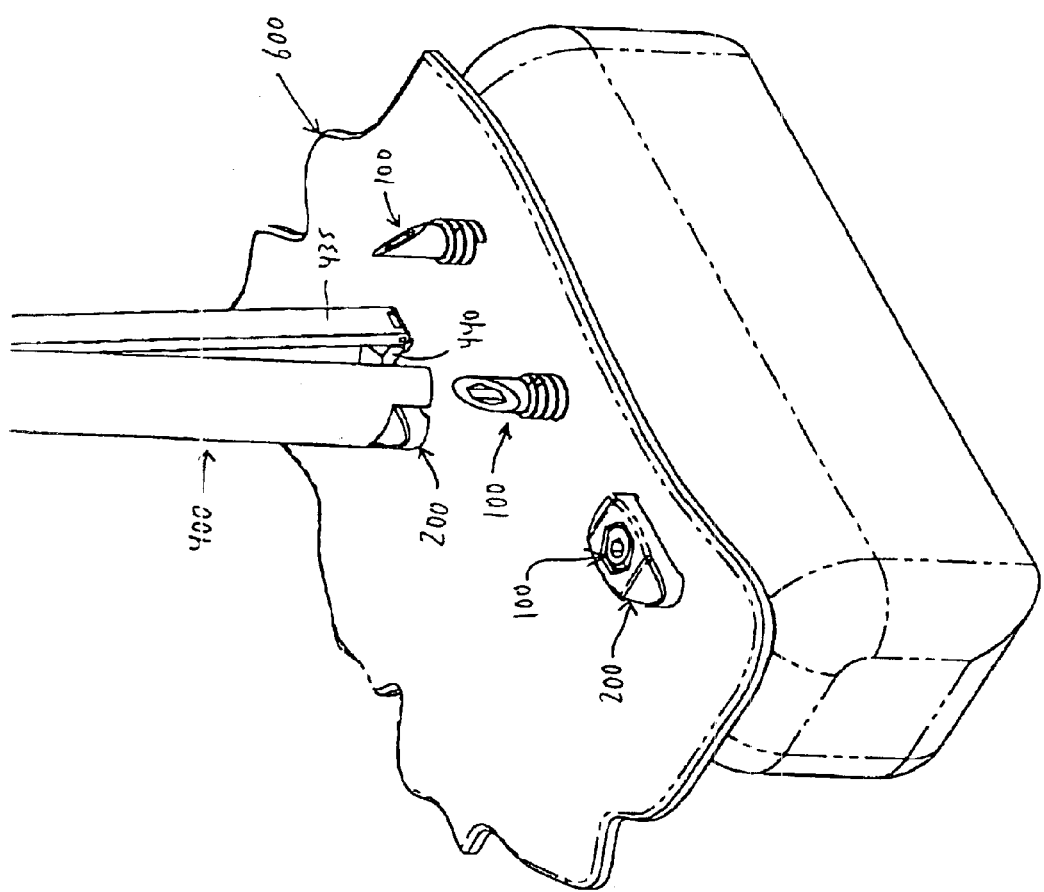
Figure 27:
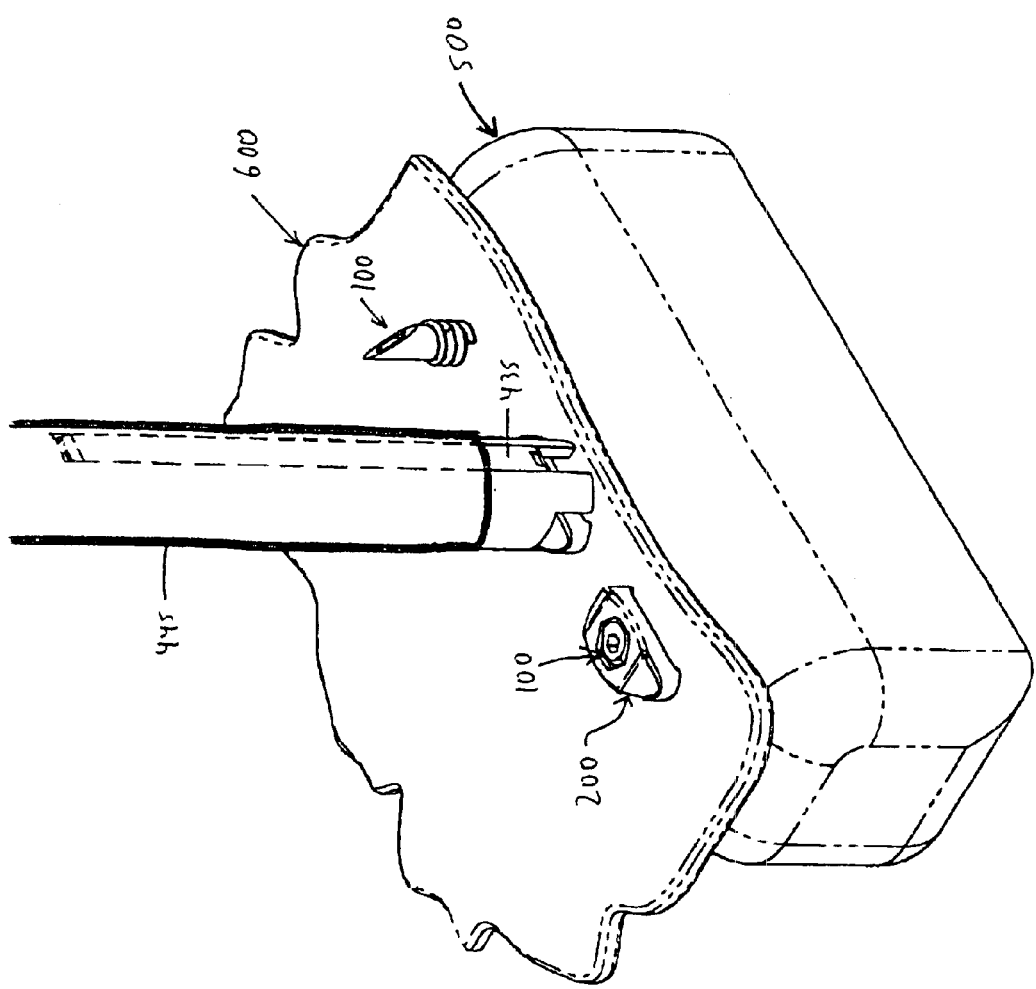
Figure 28:
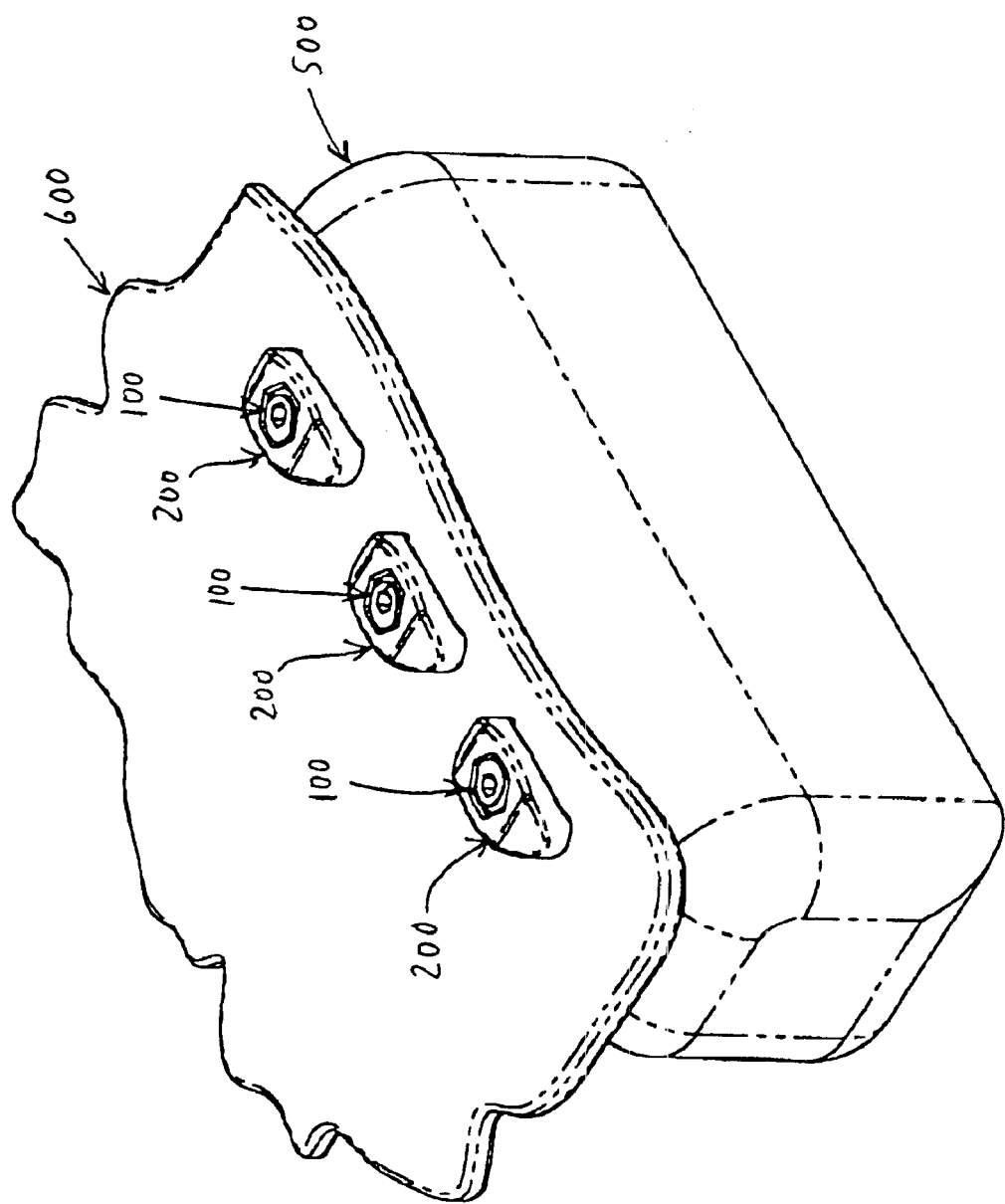

First, as shown in FIG. 22, a hole 500 is formed in a bone 505. Next, stake 100 is loaded onto the distal end of stake inserter 300 (FIG. 23) and then screwed down into the hole 500 formed in bone 505. Then stake inserter 300 is withdrawn, leaving stake 100 set in bone 505 with its sharp proximal end protruding. This process is repeated as many times as desired, until one or more stakes 100 are left protruding from bone 505 (FIG. 24). Next, a piece of soft tissue 600 is pulled over the sharp protruding proximal ends of stakes 100 and impaled on the stakes (FIG. 25). Then a cap 200 is loaded onto cap inserter 400 (FIG. 26), aligned with one of the deployed stakes 100, and then set down over the protruding sharp proximal end of the stake. As this occurs, cap 200 is forced over the proximal end of the stake, so that the cap engages threads 118 and locks thereon. Then outer tube 445 is moved distally, whereby to trim off the sharp proximal end of stake 100, leaving only cap 200 standing proud over the upper surface of the soft tissue (FIG. 28).

Figure 29:
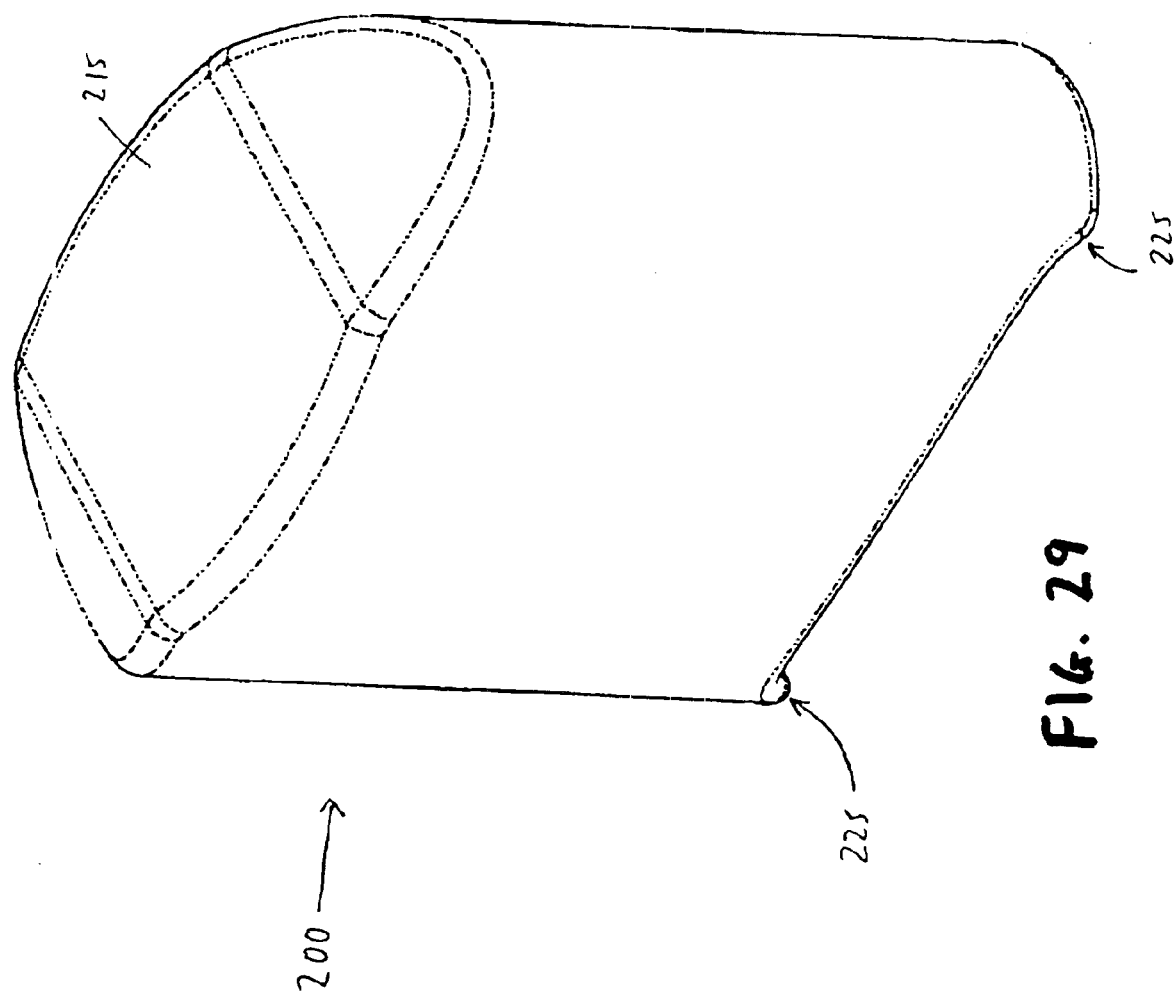
Figure 30:
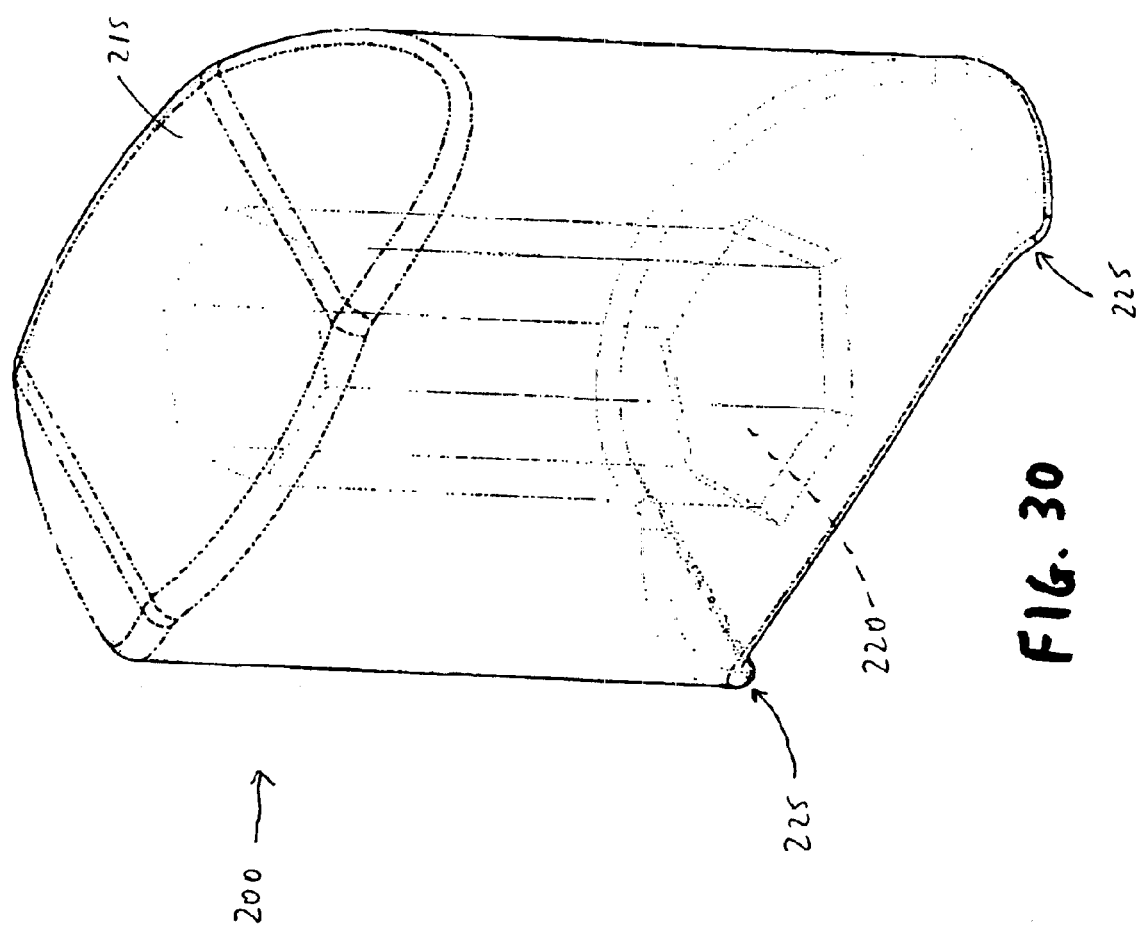
Figure 31:
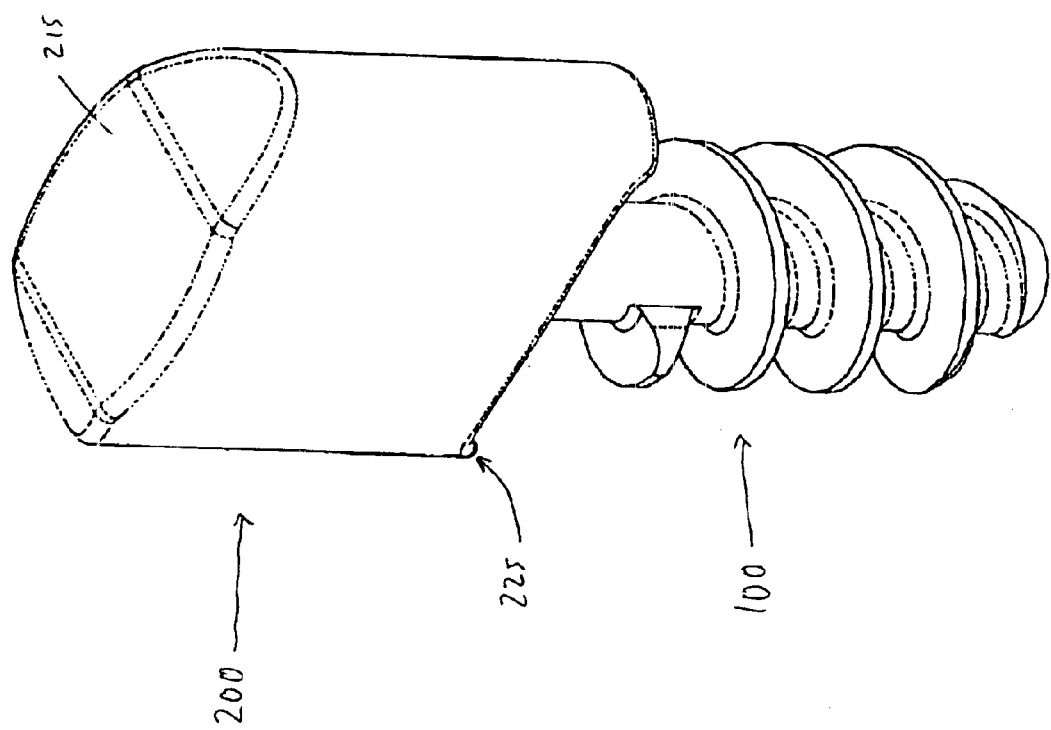

FIGS. 29–31 illustrate an alternative form of cap 200. Here, cap 200 is formed with a blind hole 220 extending proximally from its distal end. This blind hole 220 receives the sharp proximal end of stake 100, whereby cap 200 can envelope and shield the sharp proximal end of stake 100 (FIG. 31).

Stake 100 and cap 200 can be formed out of a variety of suitable biocompatible materials. In one preferred embodiment of the invention, stake 100 and cap 200 are formed out of bioabsorbable materials. In this form of the invention, stake 100 and cap 200 are preferably configured so that they absorb at different rates, with cap 200 absorbing more quickly and stake 100 absorbing more slowly. Stake 100 is preferably also configured so as to be osteogenic, i.e., so as to encourage bone ingrowth and/or remodeling. By way of example but not limitation, stake 100 may be formed out of PLA, PGA, PDS, polycaprolactone, hydroxyapetite, tricalcuim phosphate, osteogenic proteins, allograft bone, synthetic bone, etc. By way of further example but not limitation, cap 200 may be formed out of PLA, PGA, PDS, polycaprolactone, etc. In this respect it should be appreciated that by forming stake 100 so that it may be driven over substantially the entire length of the stake, such that torsional loads are spread over substantially the entire length of the stake, a broader range of materials and compositions can be used for fabricating stake 100.

What is claimed is:

1. A method for attaching tissue to a bone, the method comprising the steps of:
    embedding a distal end of a stake in the bone such that a proximal portion of the stake protrudes from the bone;
    impaling the tissue on a sharpened end of the proximal portion of the stake; and
    attaching a cap to the stake between a proximal surface of the tissue and the sharpened end of the proximal portion thereof so as to overlie the cap on the tissue.

2. The method in accordance with claim 1 wherein the stake distal end is provided with a first set of screw threads, and embedding the distal end of the stake comprises screwing the distal end of the stake into the bone.

3. The method in accordance with claim 2 wherein the stake is provided with a pointed proximal end, and impaling the tissue on the proximal portion of the stake comprises pressing the tissue onto the stake pointed end such that the pointed end penetrates the tissue.

4. The method in accordance with claim 3 wherein the stake is provided with a second set of screw threads disposed proximally of the first set of screw threads, the cap is provided with an opening threadedly engageable with the second set of screw threads, and attaching the cap to the stake comprises screwing the cap onto the stake second set of threads.

5. The method in accordance with claim 4 wherein the cap is screwed onto the stake until a distal surface of the cap engages the tissue.

6. The method in accordance with claim 1 and comprising the further step of cutting away a proximal portion of the stake extending beyond the attached cap.

7. A method for attaching tissue to a bone, the method comprising the steps of:
    embedding a distal end of a stake in the bone such that a proximal portion of the stake protrudes from the bone;
    impaling the tissue on a sharpened end of the proximal portion of the stake;
    attaching a cap to the stake so as to overlie the tissue; and
    cutting away a proximal portion of the stake extending beyond the attached cap.

8. A method for attaching tissue to a bone, the method comprising the steps of:
    embedding a distal end of a stake in the bone such that a proximal portion of the stake protrudes from the bone;
    impaling the tissue on a sharpened end of the proximal portion of the stake; and
    attaching a cap to the stake between the sharpened end of the proximal portion thereof and a proximal surface of the tissue so as to overlie the tissue;
    wherein the cap does not extend through the proximal surface of the tissue so as to position the stake and the tissue adjacent to one another.

9. A method for attaching tissue to a bone, the method comprising the steps of:
    embedding a distal end of a stake into the bone such that a proximal portion of the stake protrudes from the bone;
    impaling the tissue on a sharpened end of the proximal portion of the stake; and
    attaching a cap to the stake proximally of a proximal surface of the tissue so as to overlie the tissue;
    wherein the cap does not extend through the proximal surface of the tissue so as to position the stake and the tissue adjacent to one another.

* * * * *

UNITED STATES PATENT AND TRADEMARK OFFICE
CERTIFICATE OF CORRECTION

| | | |
|---|---|---|
| PATENT NO. | : 6,863,072 B1 | Page 1 of 1 |
| APPLICATION NO. | : 10/756445 | |
| DATED | : March 8, 2005 | |
| INVENTOR(S) | : M. Mary Sinnott | |

It is certified that error appears in the above-identified patent and that said Letters Patent is hereby corrected as shown below:

Column 5. Line 15 (detailed description) DELET "envelope" and ADD --envelop--

Signed and Sealed this

Sixth Day of March, 2007

JON W. DUDAS
*Director of the United States Patent and Trademark Office*